(12) United States Patent
Monn et al.

(10) Patent No.: US 8,318,184 B2
(45) Date of Patent: Nov. 27, 2012

(54) MGLU2 AGONISTS

(75) Inventors: James Allen Monn, Indianapolis, IN (US); Lourdes Prieto, Madrid (ES); Lorena Taboada Martinez, Barcelona (ES); Carlos Montero Salgado, Madrid (ES); Bruce William Shaw, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 22 days.

(21) Appl. No.: 12/968,352

(22) Filed: Dec. 15, 2010

(65) Prior Publication Data

US 2011/0152334 A1    Jun. 23, 2011

Related U.S. Application Data

(60) Provisional application No. 61/305,239, filed on Feb. 17, 2010.

(30) Foreign Application Priority Data

Dec. 21, 2009  (EP) .................................... 09382290

(51) Int. Cl.
  *A61K 31/35*    (2006.01)
  *A61K 39/00*    (2006.01)
  *C07D 211/78*   (2006.01)
  *C07D 249/04*   (2006.01)

(52) U.S. Cl. ..................... 424/269.1; 514/384; 514/443; 548/262.2; 548/263.2; 549/49

(58) Field of Classification Search .................. 424/269; 514/384, 443; 548/262, 263.2; 549/49
See application file for complete search history.

(56) References Cited

U.S. PATENT DOCUMENTS

| 5,688,826 A | 11/1997 | Massey et al. |
| 7,038,077 B2 * | 5/2006 | Dantzig et al. ................ 562/501 |

FOREIGN PATENT DOCUMENTS

| EP | 0 658 539 A1 | 6/1995 |
| WO | WO9717952 A1 | 5/1997 |
| WO | WO 98/51655 | 11/1998 |
| WO | WO03104217 A2 | 12/2003 |

OTHER PUBLICATIONS

Patil, S., et al., "Activiation of mGlu2/3 receptors as a new approch to treat schizophrenia: a randomized Phase 2 clinical trial," Nature Medicine, 13(9):1102-1107 and supplementary tables and figures (2007).

* cited by examiner

*Primary Examiner* — Susannah Chung
(74) *Attorney, Agent, or Firm* — Danica Hostettler; John C. Demeter

(57) ABSTRACT

The present invention provides novel mGlu2 agonists useful in the treatment of bipolar disorder, schizophrenia, depression, and generalized anxiety disorder.

35 Claims, No Drawings

MGLU2 AGONISTS

The present invention relates to mGlu2 agonist compounds, particular prodrugs thereof, and their salts and solvates and, more specifically, to novel 4-substituted bicyclo[3.1.0]hexane compounds, particular prodrugs thereof, and their salts and solvates, as well as pharmaceutical compositions and therapeutic uses of such compounds, particular prodrugs, and their salts and solvates.

L-Glutamate is the major excitatory neurotransmitter in the central nervous system and is referred to as an excitatory amino acid. The metabotropic glutamate (mGlu) receptors are G-protein-coupled receptors that modulate neuronal excitability. Treatment of neurological or psychiatric disorders has been linked to selective activation of mGlu excitatory amino acid receptors. Various studies support Group II mGlu receptor (which includes mGlu2 and/or mGlu3) activation for the treatment of schizophrenia. More particularly, recent data demonstrate that an mGlu2/3 receptor agonist has antipsychotic properties and may provide a new alternative for the treatment of schizophrenia. Studies demonstrate that the antipsychotic activity of mGlu2/3 agonists are mGlu2 mediated. Studies also demonstrate that mGlu2/3 agonists have anxiolytic, antidepressant and neuroprotective properties. Therefore, mGlu2 agonists may be useful in the treatment of psychiatric disorders, such as bipolar disorder, also known as manic depressive disorder, schizophrenia, depression, and generalized anxiety disorder.

WO9717952 discloses certain 4-substituted bicyclo[3.1.0]hexane compounds asserted to be antagonists or agonists of metabotropic glutamate receptors. WO03104217 discloses bicyclo[3.1.0]hexane and heterobicyclo[3.1.0]hexane compounds asserted to be prodrug forms of mGluR2 receptor agonist compounds.

Excessive glutamatergic tone has been implicated in many disease states of the central nervous system; however, effective agents to correct such pathophysiological states are lacking in clinical practice. In particular, clinical application has not been realized due to a lack of mGlu2 agonists with appropriate drug-like properties. Thus, there still exists a need for potent, efficacious mGlu2 agonists. The present invention provides novel 4-substituted bicyclo[3.1.0]hexanes, including particular prodrugs thereof which provide increased bioavailability suitable for clinical development, that are potent and effective mGlu2 agonists. Such new compounds of the present invention could address the need for potent, effective treatments of psychiatric disorders such as bipolar disorder, schizophrenia, depression, and generalized anxiety disorder.

The present invention provides a compound of the formula

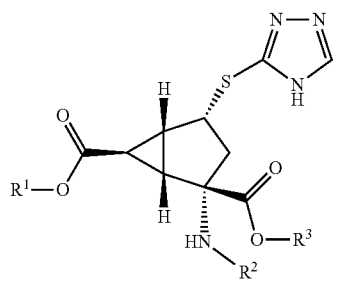

wherein
$R^1$ is hydrogen, $R^2$ is hydrogen, and $R^3$ is hydrogen;
$R^1$ is hydrogen, $R^2$ is (2S)-2-aminopropanoyl, and $R^3$ is hydrogen;
$R^1$ is hydrogen, $R^2$ is (2S)-2-amino-4-methylsulfanyl-butanoyl, and $R^3$ is hydrogen;
$R^1$ is hydrogen, $R^2$ is (2S)-2-amino-4-methyl-pentanoyl, and $R^3$ is hydrogen;
$R^1$ is hydrogen, $R^2$ is 2-aminoacetyl, and $R^3$ is hydrogen;
$R^1$ is benzyl, $R^2$ is hydrogen, and $R^3$ is benzyl; or
$R^1$ is (2-fluorophenyl)methyl, $R^2$ is hydrogen, and $R^3$ is (2-fluorophenyl)methyl;
or a pharmaceutically acceptable salt thereof or a solvate of the salt.

The present invention provides (1R,2S,4R,5R,6R)-2-amino-4-(4H-1,2,4-triazol-3-ylsulfanyl)bicyclo[3.1.0]hexane-2,6-dicarboxylic acid, or a pharmaceutically acceptable salt thereof.

As a particular embodiment, the present invention provides (1R,2S,4R,5R,6R)-2-amino-4-(4H-1,2,4-triazol-3-ylsulfanyl)bicyclo[3.1.0]hexane-2,6-dicarboxylic acid.

The present invention provides (1R,2S,4R,5R,6R)-2-[[(2S)-2-aminopropanoyl]amino]-4-(1H-1,2,4-triazol-3-ylsulfanyl)bicyclo[3.1.0]hexane-2,6-dicarboxylic acid, or a pharmaceutically acceptable salt thereof.

As a particular embodiment, the present invention provides (1R,2S,4R,5R,6R)-2-[[(2S)-2-aminopropanoyl]amino]-4-(1H-1,2,4-triazol-3-ylsulfanyl)bicyclo[3.1.0]hexane-2,6-dicarboxylic acid hydrochloride.

The present invention provides (1R,2S,4R,5R,6R)-2-[[(2S)-2-amino-4-methylsulfanyl-butanoyl]amino]-4-(4H-1,2,4-triazol-3-ylsulfanyl)bicyclo[3.1.0]hexane-2,6-dicarboxylic acid, or a pharmaceutically acceptable salt thereof.

As a particular embodiment, the present invention provides (1R,2S,4R,5R,6R)-2-[[(2S)-2-amino-4-methylsulfanyl-butanoyl]amino]-4-(4H-1,2,4-triazol-3-ylsulfanyl)bicyclo[3.1.0]hexane-2,6-dicarboxylic acid hydrochloride.

The present invention provides (1R,2S,4R,5R,6R)-2-[[(2S)-2-amino-4-methyl-pentanoyl]amino]-4-(4H-1,2,4-triazol-3-ylsulfanyl)bicyclo[3.1.0]hexane-2,6-dicarboxylic acid, or a pharmaceutically acceptable salt thereof.

As a particular embodiment, the present invention provides (1R,2S,4R,5R,6R)-2-[[(2S)-2-amino-4-methyl-pentanoyl]amino]-4-(4H-1,2,4-triazol-3-ylsulfanyl)bicyclo[3.1.0]hexane-2,6-dicarboxylic acid hydrochloride.

The present invention provides (1R,2S,4R,5R,6R)-2-[(2-aminoacetyl)amino]-4-(4H-1,2,4-triazol-3-ylsulfanyl)bicyclo[3.1.0]hexane-2,6-dicarboxylic acid, or a pharmaceutically acceptable salt thereof.

As a particular embodiment, the present invention provides (1R,2S,4R,5R,6R)-2-[(2-aminoacetyl)amino]-4-(4H-1,2,4-triazol-3-ylsulfanyl)bicyclo[3.1.0]hexane-2,6-dicarboxylic acid hydrochloride.

The present invention provides dibenzyl (1R,2S,4R,5R,6R)-2-amino-4-(4H-1,2,4-triazol-3-ylsulfanyl)bicyclo[3.1.0]hexane-2,6-dicarboxylate, or a pharmaceutically acceptable salt thereof.

As a particular embodiment, the present invention provides dibenzyl (1R,2S,4R,5R,6R)-2-amino-4-(4H-1,2,4-triazol-3-ylsulfanyl)bicyclo[3.1.0]hexane-2,6-dicarboxylate.

The present invention provides bis[(2-fluorophenyl)methyl](1R,2S,4R,5R,6R)-2-amino-4-(4H-1,2,4-triazol-3-ylsulfanyl)bicyclo[3.1.0]hexane-2,6-dicarboxylate, or a pharmaceutically acceptable salt thereof.

As a particular embodiment, the present invention provides bis[(2-fluorophenyl)methyl](1R,2S,4R,5R,6R)-2-amino-4-(4H-1,2,4-triazol-3-ylsulfanyl)bicyclo[3.1.0]hexane-2,6-dicarboxylate hydrochloride.

The present invention provides bicyclo[3.1.0]hexane-2,6-dicarboxylic acid, 2-[[(2S)-2-amino-1-oxopropyl]amino]-4-(4H-1,2,4-triazol-3-ylthio)-, monoammonium salt, (1R,2S,4R,5R,6R)—, monohydrate.

The present invention provides bicyclo[3.1.0]hexane-2,6-dicarboxylic acid, 2-[[(2S)-2-amino-1-oxopropyl]amino]-4-(4H-1,2,4-triazol-3-ylthio)-, monoammonium salt, (1R,2S,4R,5R,6R)—, monohydrate in crystalline form.

The present invention provides bicyclo[3.1.0]hexane-2,6-dicarboxylic acid, 2-[[(2S)-2-amino-1-oxopropyl]amino]-4-(4H-1,2,4-triazol-3-ylthio)-, monoammonium salt, (1R,2S,4R,5R,6R)—, monohydrate in crystalline form characterized by a X-ray powder diffraction pattern having peaks at 2θ±0.2 equal to 18.61 and 21.07.

The present invention also provides bicyclo[3.1.0]hexane-2,6-dicarboxylic acid, 2-[[(2S)-2-amino-1-oxopropyl]amino]-4-(4H-1,2,4-triazol-3-ylthio)-, monoammonium salt, (1R,2S,4R,5R,6R)—, monohydrate in crystalline form characterized by a X-ray powder diffraction pattern having peaks at 2θ±0.2 at 18.61 in combination with one or more of the peaks selected from the group consisting of 21.07, 15.34, 14.74, and 19.20.

Compounds of the present invention are (1R,2S,4R,5R,6R)-2-amino-4-(4H-1,2,4-triazol-3-ylsulfanyl)bicyclo[3.1.0]hexane-2,6-dicarboxylic acid, (1R,2S,4R,5R,6R)-2-[[(2S)-2-aminopropanoyl]amino]-4-(1H-1,2,4-triazol-3-ylsulfanyl)bicyclo[3.1.0]hexane-2,6-dicarboxylic acid, (1R,2S,4R,5R,6R)-2-[[(2S)-2-amino-4-methylsulfanyl-butanoyl]amino]-4-(4H-1,2,4-triazol-3-ylsulfanyl)bicyclo[3.1.0]hexane-2,6-dicarboxylic acid, (1R,2S,4R,5R,6R)-2-[[(2S)-2-amino-4-methyl-pentanoyl]amino]-4-(4H-1,2,4-triazol-3-ylsulfanyl)bicyclo[3.1.0]hexane-2,6-dicarboxylic acid, (1R,2S,4R,5R,6R)-2-[(2-aminoacetyl)amino]-4-(4H-1,2,4-triazol-3-ylsulfanyl)bicyclo[3.1.0]hexane-2,6-dicarboxylic acid, dibenzyl (1R,2S,4R,5R,6R)-2-amino-4-(4H-1,2,4-triazol-3-ylsulfanyl)bicyclo[3.1.0]hexane-2,6-dicarboxylate, and/or bis[(2-fluorophenyl)methyl](1R,2S,4R,5R,6R)-2-amino-4-(4H-1,2,4-triazol-3-ylsulfanyl)bicyclo[3.1.0]hexane-2,6-dicarboxylate, or a pharmaceutically acceptable salt thereof.

The present invention provides a pharmaceutical composition comprising (1R,2S,4R,5R,6R)-2-amino-4-(4H-1,2,4-triazol-3-ylsulfanyl)bicyclo[3.1.0]hexane-2,6-dicarboxylic acid, or a pharmaceutically acceptable salt thereof, (1R,2S,4R,5R,6R)-2-[[(2S)-2-aminopropanoyl]amino]-4-(1H-1,2,4-triazol-3-ylsulfanyl)bicyclo[3.1.0]hexane-2,6-dicarboxylic acid, or a pharmaceutically acceptable salt thereof, (1R,2S,4R,5R,6R)-2-[[(2S)-2-amino-4-methylsulfanyl-butanoyl]amino]-4-(4H-1,2,4-triazol-3-ylsulfanyl)bicyclo[3.1.0]hexane-2,6-dicarboxylic acid, or a pharmaceutically acceptable salt thereof, (1R,2S,4R,5R,6R)-2-[[(2S)-2-amino-4-methyl-pentanoyl]amino]-4-(4H-1,2,4-triazol-3-ylsulfanyl)bicyclo[3.1.0]hexane-2,6-dicarboxylic acid, or a pharmaceutically acceptable salt thereof, (1R,2S,4R,5R,6R)-2-[(2-aminoacetyl)amino]-4-(4H-1,2,4-triazol-3-ylsulfanyl)bicyclo[3.1.0]hexane-2,6-dicarboxylic acid, or a pharmaceutically acceptable salt thereof, dibenzyl (1R,2S,4R,5R,6R)-2-amino-4-(4H-1,2,4-triazol-3-ylsulfanyl)bicyclo[3.1.0]hexane-2,6-dicarboxylate, or a pharmaceutically acceptable salt thereof, bis[(2-fluorophenyl)methyl](1R,2S,4R,5R,6R)-2-amino-4-(4H-1,2,4-triazol-3-ylsulfanyl)bicyclo[3.1.0]hexane-2,6-dicarboxylate, or a pharmaceutically acceptable salt thereof, or bicyclo[3.1.0]hexane-2,6-dicarboxylic acid, 2-[[(2S)-2-amino-1-oxopropyl]amino]-4-(4H-1,2,4-triazol-3-ylthio)-, monoammonium salt, (1R,2S,4R,5R,6R)—, monohydrate, together with a pharmaceutically acceptable carrier and optionally other therapeutic ingredients.

The present invention provides a pharmaceutical composition comprising (1R,2S,4R,5R,6R)-2-amino-4-(4H-1,2,4-triazol-3-ylsulfanyl)bicyclo[3.1.0]hexane-2,6-dicarboxylic acid, or a pharmaceutically acceptable salt thereof, (1R,2S,4R,5R,6R)-2-[[(2S)-2-aminopropanoyl]amino]-4-(1H-1,2,4-triazol-3-ylsulfanyl)bicyclo[3.1.0]hexane-2,6-dicarboxylic acid, or a pharmaceutically acceptable salt thereof, (1R,2S,4R,5R,6R)-2-[[(2S)-2-amino-4-methylsulfanyl-butanoyl]amino]-4-(4H-1,2,4-triazol-3-ylsulfanyl)bicyclo[3.1.0]hexane-2,6-dicarboxylic acid, or a pharmaceutically acceptable salt thereof, (1R,2S,4R,5R,6R)-2-[[(2S)-2-amino-4-methyl-pentanoyl]amino]-4-(4H-1,2,4-triazol-3-ylsulfanyl)bicyclo[3.1.0]hexane-2,6-dicarboxylic acid, or a pharmaceutically acceptable salt thereof, (1R,2S,4R,5R,6R)-2-[(2-aminoacetyl)amino]-4-(4H-1,2,4-triazol-3-ylsulfanyl)bicyclo[3.1.0]hexane-2,6-dicarboxylic acid, or a pharmaceutically acceptable salt thereof, dibenzyl (1R,2S,4R,5R,6R)-2-amino-4-(4H-1,2,4-triazol-3-ylsulfanyl)bicyclo[3.1.0]hexane-2,6-dicarboxylate, or a pharmaceutically acceptable salt thereof, bis[(2-fluorophenyl)methyl](1R,2S,4R,5R,6R)-2-amino-4-(4H-1,2,4-triazol-3-ylsulfanyl)bicyclo[3.1.0]hexane-2,6-dicarboxylate, or a pharmaceutically acceptable salt thereof, or bicyclo[3.1.0]hexane-2,6-dicarboxylic acid, 2-[[(2S)-2-amino-1-oxopropyl]amino]-4-(4H-1,2,4-triazol-3-ylthio)-, monoammonium salt, (1R,2S,4R,5R,6R)—, monohydrate, and a pharmaceutically acceptable carrier, diluent, or excipient.

The present invention provides a method of treating a psychiatric disorder, comprising administering to a patient in need thereof an effective amount of (1R,2S,4R,5R,6R)-2-amino-4-(4H-1,2,4-triazol-3-ylsulfanyl)bicyclo[3.1.0]hexane-2,6-dicarboxylic acid, or a pharmaceutically acceptable salt thereof, (1R,2S,4R,5R,6R)-2-[[(2S)-2-aminopropanoyl]amino]-4-(1H-1,2,4-triazol-3-ylsulfanyl)bicyclo[3.1.0]hexane-2,6-dicarboxylic acid, or a pharmaceutically acceptable salt thereof, (1R,2S,4R,5R,6R)-2-[[(2S)-2-amino-4-methylsulfanyl-butanoyl]amino]-4-(4H-1,2,4-triazol-3-ylsulfanyl)bicyclo[3.1.0]hexane-2,6-dicarboxylic acid, or a pharmaceutically acceptable salt thereof, (1R,2S,4R,5R,6R)-2-[[(2S)-2-amino-4-methyl-pentanoyl]amino]-4-(4H-1,2,4-triazol-3-ylsulfanyl)bicyclo[3.1.0]hexane-2,6-dicarboxylic acid, or a pharmaceutically acceptable salt thereof, (1R,2S,4R,5R,6R)-2-[(2-aminoacetyl)amino]-4-(4H-1,2,4-triazol-3-ylsulfanyl)bicyclo[3.1.0]hexane-2,6-dicarboxylic acid, or a pharmaceutically acceptable salt thereof, dibenzyl (1R,2S,4R,5R,6R)-2-amino-4-(4H-1,2,4-triazol-3-ylsulfanyl)bicyclo[3.1.0]hexane-2,6-dicarboxylate, or a pharmaceutically acceptable salt thereof, bis[(2-fluorophenyl)methyl](1R,2S,4R,5R,6R)-2-amino-4-(4H-1,2,4-triazol-3-ylsulfanyl)bicyclo[3.1.0]hexane-2,6-dicarboxylate, or a pharmaceutically acceptable salt thereof, or bicyclo[3.1.0]hexane-2,6-dicarboxylic acid, 2-[[(2S)-2-amino-1-oxopropyl]amino]-4-(4H-1,2,4-triazol-3-ylthio)-, monoammonium salt, (1R,2S,4R,5R,6R)—, monohydrate.

The present invention provides the use of (1R,2S,4R,5R,6R)-2-amino-4-(4H-1,2,4-triazol-3-ylsulfanyl)bicyclo[3.1.0]hexane-2,6-dicarboxylic acid, or a pharmaceutically acceptable salt thereof, (1R,2S,4R,5R,6R)-2-[[(2S)-2-aminopropanoyl]amino]-4-(1H-1,2,4-triazol-3-ylsulfanyl)bicyclo[3.1.0]hexane-2,6-dicarboxylic acid, or a pharmaceutically acceptable salt thereof, (1R,2S,4R,5R,6R)-2-[[(2S)-2-amino-4-methylsulfanyl-butanoyl]amino]-4-(4H-1,2,4-triazol-3-ylsulfanyl)bicyclo[3.1.0]hexane-2,6-dicarboxylic acid, or a pharmaceutically acceptable salt thereof, (1R,2S,4R,5R,6R)-2-[[(2S)-2-amino-4-methyl-pentanoyl]amino]-4-(4H-1,2,4-triazol-3-ylsulfanyl)bicyclo[3.1.0]hexane-2,6-dicarboxylic acid, or a pharmaceutically acceptable salt thereof, (1R,2S,4R,5R,6R)-2-[(2-aminoacetyl)amino]-4-(4H-1,2,4-triazol-3-ylsulfanyl)bicyclo[3.1.0]hexane-2,6-dicarboxylic acid, or a pharmaceutically acceptable salt thereof, dibenzyl (1R,2S,4R,5R,6R)-2-amino-4-(4H-1,2,4-triazol-3-ylsulfanyl)bicyclo[3.1.0]hexane-2,6-dicarboxylate, or a pharmaceutically acceptable salt thereof, bis[(2- fluorophenyl)methyl](1R,2S,4R,5R,6R)-2-amino-4-(4H-1,2,4-triazol-3-ylsulfanyl)bicyclo[3.1.0]hexane-2,6-dicarboxylate, or a pharmaceutically acceptable salt thereof, or bicyclo[3.1.0]hexane-2,6-dicarboxylic acid, 2-[[(2S)-2-amino-1-oxopropyl]amino]-4-(4H-1,2,4-triazol-3-ylthio)-, monoammonium salt, (1R,2S,4R,5R,6R)—, monohydrate, for the manufacture of a medicament for the treatment of a psychiatric disorder.

The present invention provides (1R,2S,4R,5R,6R)-2-amino-4-(4H-1,2,4-triazol-3-ylsulfanyl)bicyclo[3.1.0]hexane-2,6-dicarboxylic acid, or a pharmaceutically acceptable salt thereof, (1R,2S,4R,5R,6R)-2-[[(2S)-2-aminopropanoyl]amino]-4-(1H-1,2,4-triazol-3-ylsulfanyl)bicyclo[3.1.0]hexane-2,6-dicarboxylic acid, or a pharmaceutically acceptable salt thereof, (1R,2S,4R,5R,6R)-2-[[(2S)-2-amino-4-methylsulfanyl-butanoyl]amino]-4-(4H-1,2,4-triazol-3-ylsulfanyl)bicyclo[3.1.0]hexane-2,6-dicarboxylic acid, or a pharmaceutically acceptable salt thereof, (1R,2S,4R,5R,6R)-2-[[(2S)-2-amino-4-methyl-pentanoyl]amino]-4-(4H-1,2,4-triazol-3-ylsulfanyl)bicyclo[3.1.0]hexane-2,6-dicarboxylic acid, or a pharmaceutically acceptable salt thereof, (1R,2S,4R,5R,6R)-2-[(2-aminoacetyl)amino]-4-(4H-1,2,4-triazol-3-ylsulfanyl)bicyclo[3.1.0]hexane-2,6-dicarboxylic acid, or a pharmaceutically acceptable salt thereof, dibenzyl (1R,2S,4R,5R,6R)-2-amino-4-(4H-1,2,4-triazol-3-ylsulfanyl)bicyclo[3.1.0]hexane-2,6-dicarboxylate, or a pharmaceutically acceptable salt thereof, bis[(2-fluorophenyl)methyl](1R,2S,4R,5R,6R)-2-amino-4-(4H-1,2,4-triazol-3-ylsulfanyl)bicyclo[3.1.0]hexane-2,6-dicarboxylate, or a pharmaceutically acceptable salt thereof, or bicyclo[3.1.0]hexane-2,6-dicarboxylic acid, 2-[[(2S)-2-amino-1-oxopropyl]amino]-4-(4H-1,2,4-triazol-3-ylthio)-, monoammonium salt, (1R,2S,4R,5R,6R)—, monohydrate, for use in therapy. The present invention also provides (1R,2S,4R,5R,6R)-2-amino-4-(4H-1,2,4-triazol-3-ylsulfanyl)bicyclo[3.1.0]hexane-2,6-dicarboxylic acid, or a pharmaceutically acceptable salt thereof, (1R,2S,4R,5R,6R)-2-[[(2S)-2-aminopropanoyl]amino]-4-(1H-1,2,4-triazol-3-ylsulfanyl)bicyclo[3.1.0]hexane-2,6-dicarboxylic acid, or a pharmaceutically acceptable salt thereof, (1R,2S,4R,5R,6R)-2-[[(2S)-2-amino-4-methylsulfanyl-butanoyl]amino]-4-(4H-1,2,4-triazol-3-ylsulfanyl)bicyclo[3.1.0]hexane-2,6-dicarboxylic acid, or a pharmaceutically acceptable salt thereof, (1R,2S,4R,5R,6R)-2-[[(2S)-2-amino-4-methyl-pentanoyl]amino]-4-(4H-1,2,4-triazol-3-ylsulfanyl)bicyclo[3.1.0]hexane-2,6-dicarboxylic acid, or a pharmaceutically acceptable salt thereof, (1R,2S,4R,5R,6R)-2-[(2-aminoacetyl)amino]-4-(4H-1,2,4-triazol-3-ylsulfanyl)bicyclo[3.1.0]hexane-2,6-dicarboxylic acid, or a pharmaceutically acceptable salt thereof, dibenzyl (1R,2S,4R,5R,6R)-2-amino-4-(4H-1,2,4-triazol-3-ylsulfanyl)bicyclo[3.1.0]hexane-2,6-dicarboxylate, or a pharmaceutically acceptable salt thereof, bis[(2-fluorophenyl)methyl](1R,2S,4R,5R,6R)-2-amino-4-(4H-1,2,4-triazol-3-ylsulfanyl)bicyclo[3.1.0]hexane-2,6-dicarboxylate, or a pharmaceutically acceptable salt thereof, or bicyclo[3.1.0]hexane-2,6-dicarboxylic acid, 2-[[(2S)-2-amino-1-oxopropyl]amino]-4-(4H-1,2,4-triazol-3-ylthio)-, monoammonium salt, (1R,2S,4R,5R,6R)—, monohydrate, for use in the treatment of a psychiatric disorder.

Furthermore, the present invention provides preferred embodiments of the methods and uses as described herein, in which the psychiatric disorder is selected from the group consisting of bipolar disorder, schizophrenia, depression, and generalized anxiety disorder.

As used above, and throughout the description of the invention, the following terms, unless otherwise indicated, shall be understood to have the following meanings:

"Pharmaceutically acceptable salts" refers to the relatively non-toxic, inorganic and organic salts of compounds of the present invention.

"Therapeutically effective amount" or "effective amount" means the amount of the compound, or pharmaceutically acceptable salt thereof or a solvate of the salt, of the present invention or pharmaceutical composition containing a compound, or pharmaceutically acceptable salt thereof or a solvate of the salt, of the present invention that will elicit the biological or medical response of or desired therapeutic effect on a tissue, system, animal, mammal or human that is being sought by the researcher, veterinarian, medical doctor or other clinician.

The terms "treatment," "treat," "treating," and the like, are meant to include slowing or reversing the progression of a disorder. These terms also include alleviating, ameliorating, attenuating, eliminating, or reducing one or more symptoms of a disorder or condition, even if the disorder or condition is not actually eliminated and even if progression of the disorder or condition is not itself slowed or reversed.

Under standard nomenclature used throughout this disclosure, the terminal portion of the designated side chain is described first, followed by the adjacent functionality toward the point of attachment. For example, a methylsulfonyl substituent is equivalent to $CH_3$—$SO_2$—.

The compounds of the present invention are capable of reaction, for example, with a number of inorganic and organic acids to form pharmaceutically acceptable acid addition salts or basic addition salts. Such pharmaceutically acceptable salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol. 66, No. 1, January 1977.

The compounds of the present invention are preferably formulated as pharmaceutical compositions using one or more pharmaceutically acceptable carriers, diluents, or excipients and administered by a variety of routes. Preferably, such compositions are for oral or intravenous administration. Such pharmaceutical compositions and processes for preparing them are well known in the art. See, e.g., Remington: The Science and Practice of Pharmacy (A. Gennaro, et al., eds., 21st ed., Mack Publishing Co., 2005).

The compound or compounds of the present invention actually administered will be determined by a physician under the relevant circumstances, including the condition to be treated, the chosen route of administration, the actual compound or compounds of the present invention administered, the age, weight, and response of the individual patient, and the severity of the patient's symptoms. Dosages per day normally fall within the range of about 0.1 to about 300 mg. In some instances dosage levels below the lower limit of the aforesaid range may be more than adequate, while in other cases still larger doses may be employed.

The compounds of the present invention may be prepared by a variety of procedures known in the art, as well as those described in the Preparations and Examples below. The specific synthetic steps for each of the routes described may be combined in different ways to prepare the compounds of the present invention.

The substituents, unless otherwise indicated, are as previously defined. The reagents and starting materials are generally readily available to one of ordinary skill in the art. Others may be made by standard techniques of organic and heterocyclic chemistry, techniques which are analogous to the syntheses of known structurally similar compounds and the procedures described in the Preparations and Examples which follow including any novel procedures. The naming of the following Preparations and Examples 1 through 7 is done using Symyx Draw 3.1. The naming of Example 8 is done using the CAS name from ACD Labs.

As used herein, the following terms have the meanings indicated: "HPLC" refers to high-pressure liquid chromatography; "LC" refers to liquid chromatography; "MS" refers to mass spectroscopy; "NMR" refers to nuclear magnetic resonance; "TLC" refers to thin layer chromatography; "EDTA" refers to ethylenediaminetetraacetic acid; "PBS" refers to phosphate buffered saline; "PCR" refers to polymerase chain reaction; "SCX" refers to strong cation exchange; and "HLB" refers to hydrophilic-lipophilic balance.

Preparation 1

Ditert-butyl (1S,2S,4S,5R,6R)-2-(tert-butoxycarbonylamino)-4-(p-tolylsulfonyloxy) bicyclo[3.1.0]hexane-2,6-dicarboxylate

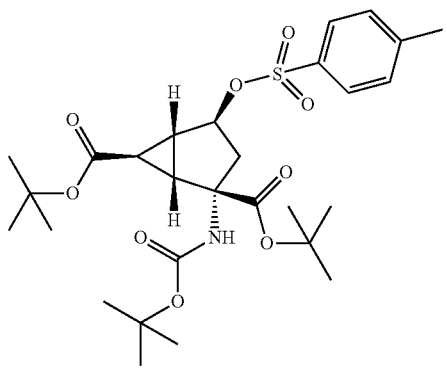

Charge a 2-necked round bottom flask under nitrogen atmosphere with ditert-butyl (1S,2S,4S,5R,6R)-2-(tert-butoxycarbonylamino)-4-hydroxy-bicyclo[3.1.0]hexane-2,6-dicarboxylate (20.7 g, 0.5 mol, see WO03/104217/A2 for synthesis details), 4-dimethylaminopyridine (10.4 g, 0.85 mol), triethylamine (6.98 mL, 0.5 mmol) and p-toluenesulfonyl chloride (10.6 g, 0.55 mol) in dichloromethane (200 mL), and stir the mixture at room temperature overnight. Add 1N solution of potassium hydrogen sulfate (200 mL), water (100 mL) and extract the organic layer. Wash with water (200 mL), brine (200 mL), dry over magnesium sulfate, filter and evaporate to dryness. Add tetrahydrofuran (30 mL) then heptanes (90 mL). Heat the mixture at 60° C. and slowly add more heptanes (200 mL). Cool the mixture to room temperature. Filter the solid and dry in vacuo to yield the title compound as a white solid (24.6 g, 87%). MS (m/z): 590 (M+23).

Preparation 2

Ditert-butyl (1R,2S,4R,5R,6R)-2-(tert-butoxycarbonylamino)-4-(4H-1,2,4-triazol-3-ylsulfanyl)bicyclo[3.1.0]hexane-2,6-dicarboxylate

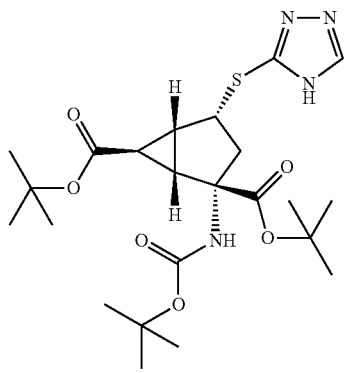

Method 1:

Charge under nitrogen atmosphere a round bottom flask with ditert-butyl (1S,2S,4S,5R,6R)-2-(tert-butoxycarbonylamino)-4-(p-tolylsulfonyloxy) bicyclo[3.1.0]hexane-2,6-dicarboxylate (462 g, 813.8 mmol), 1H-1,2,4-triazole-3-thiol (88.2 g, 854.5 mmol), potassium carbonate (123.7 g, 895.2 mmol) in N,N-dimethylformamide (2.3 L) and stir the mixture at 80° C. for 2 hours. Cool the reaction mixture to room temperature then add methyl-t-butyl ether (2.3 L) and water (4.6 L). Observe gas evolution following the slow addition of 1M potassium hydrogen sulfate (1.85 L). Extract the mixture with methyl-t-butyl ether (2.3 L) and discard the aqueous phase. Wash successively with water (2.5 L), brine (2 L) and discard the aqueous phases. Concentrate to dryness to give a solid (440 g). Purify by flash chromatography eluting with ethyl acetate:hexane (20:80 to 70:30) to yield the title compound as a white solid (305.6 g, 76%). MS (m/z): 497 (M+1).

Method 2:

Dissolve ditert-butyl (1S,2S,4S,5R,6R)-2-(tert-butoxycarbonylamino)-4-(p-tolylsulfonyloxy) bicyclo[3.1.0]hexane-2,6-dicarboxylate (1.31 g, 2.31 mmol) and 1H-1,2,4-triazole-3-thiol (0.31 g, 3 mmol) in N,N-dimethylformamide (7 mL), then add potassium carbonate (639 mg, 4.62 mmol) and stir the mixture overnight at 80° C. Concentrate to dryness, redissolve in ethyl acetate, and wash with 10% citric acid solution and 10% brine. Dry over sodium sulfate, filter and concentrate to dryness. Purify by flash chromatography eluting with ethyl acetate:hexane (10:90 to 80:20) to yield the title compound (830 mg, 72%). MS (m/z): 497 (M+1)

Preparation 3

Diethyl(1R,2S,4R,5R,6R)-2-amino-4-(4H-1,2,4-triazol-3-ylsulfanyl)bicyclo[3.1.0]hexane-2,6-dicarboxylate hydrochloride

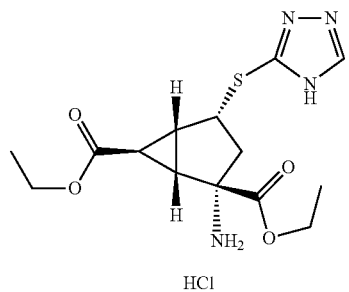

Method 1:

Charge a round bottom flask with ditert-butyl (1R,2S,4R,5R,6R)-2-(tert-butoxycarbonylamino)-4-(4H-1,2,4-triazol-3-ylsulfanyl)bicyclo[3.1.0]hexane-2,6-dicarboxylate (305.6 g, 0.61 mol) and ethanol (1.53 L). Add slowly thionyl chloride (179.3 mL, 2.46 mol) (exothermic reaction to 45° C.) and stir the mixture at 80° C. overnight. Remove the solvent under vacuum to give a white foam. Add methyl-t-butyl ether (2.5 L) and remove the solvent under vacuum. Add methyl-t-butyl ether (2.5 L) and stir overnight. Filter the solid and wash with methyl-t-butyl ether. Dry under a nitrogen blanket to give the title compound as a white solid (264.6 g, 0.7 mol). MS (m/z): 341 (M+1).

Method 2:

Dissolve ditert-butyl (1R,2S,4R,5R,6R)-2-(tert-butoxycarbonylamino)-4-(4H-1,2,4-triazol-3-ylsulfanyl)bicyclo[3.1.0]hexane-2,6-dicarboxylate (830 mg, 1.67 mmol) in ethanol (6.7 mL), cool the mixture to 5° C. and add thionyl chloride (487 µL, 6.69 mmol). Heat the mixture at 80° C. overnight. Remove the solvent under vacuum to give a white solid then add diethyl ether and concentrate to dryness. Dry the material further for 48 hours to give the title compound (714 mg, 1.89 mmol). MS (m/z): 341 (M+1).

Preparation 4

Diethyl(1R,2S,4R,5R,6R)-2-[[(2S)-2-(tert-butoxycarbonylamino)propanoyl]amino]-4-(4H-1,2,4-triazol-3-ylsulfanyl)bicyclo[3.1.0]hexane-2,6-dicarboxylate

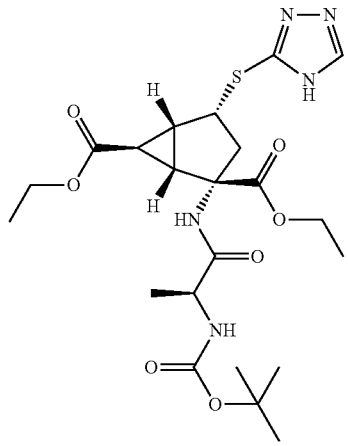

Method 1:

To a 5 L reactor under nitrogen atmosphere, add diethyl (1R,2S,4R,5R,6R)-2-amino-4-(4H-1,2,4-triazol-3-ylsulfanyl)bicyclo[3.1.0]hexane-2,6-dicarboxylate hydrochloride (264 g, 0.7 mol) and tetrahydrofuran (1.32 L) and cool the mixture to 0-5° C. with an ice water bath. Then add chlorodimethoxytriazine (125.5 g, 0.7 mol) and (2S)-2-(tert-butoxycarbonylamino)propanoic acid (141.3 g, 0.73 mol). Slowly add N-methylmorpholine (231.8 mL, 2.1 mol) and stir for 3 hours. Filter the mixture and wash the white solid with tetrahydrofuran. Discard the solid and concentrate the solution to dryness. Purify by flash chromatography eluting with ethyl acetate:hexane (60:40 to 100:0) to yield the title compound (195 g, 54%). MS (m/z): 512 (M+1), 534 (M+23).

Method 2:

Combine diethyl (1R,2S,4R,5R,6R)-2-amino-4-(4H-1,2,4-triazol-3-ylsulfanyl)bicyclo[3.1.0]hexane-2,6-dicarboxylate hydrochloride (354 mg, 0.94 mmol), (2S)-2-(tert-butoxycarbonylamino)propanoic acid (271 mg, 1.41 mmol), 4-dimethylaminopyridine (11.5 mg, 94 μmol), 1-hydroxybenzotriazole hydrate (219 mg, 1.41 mmol) and 1-(3-dimethylaminopropyl)-3-ethylcarbodiimide hydrochloride (274 mg, 1.41 mmol) in dichloromethane (9.4 mL) then add triethylamine (393 μL, 2.82 mmol) and stir the mixture at room temperature overnight under a nitrogen atmosphere. Wash with 10% citric acid solution, saturated sodium hydrogen carbonate solution and brine. Discard the aqueous layers, filter the organic layer through a diatomaceous earth cartridge and remove the solvent under vacuum. Purify by flash chromatography eluting with ethyl acetate:hexane (20:80 to 100:0) to yield the title compound (319 mg, 66%). MS (m/z): 512 (M+1), 534 (M+23).

The following compounds are prepared essentially following method 1 of preparation 4.

| Prep No. | Chemical name | Structure | Physical data |
|---|---|---|---|
| 5 | Diethyl (1R,2S,4R,5R,6R)-2-[[(2S)-2-(tert-butoxycarbonylamino)-4-methylsulfanyl-butanoyl]amino]-4-(4H-1,2,4-triazol-3-ylsulfanyl)bicyclo[3.1.0]hexane-2,6-dicarboxylate | 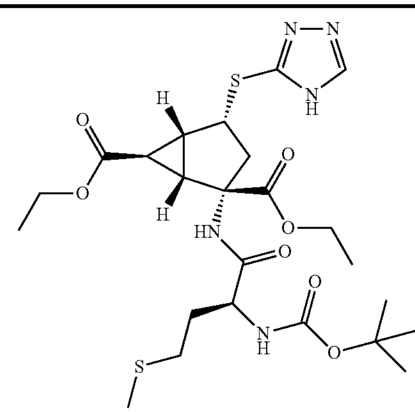 | MS (m/z): 572 (M + 1), 594 (M + 23). |
| 6 | Diethyl (1R,2S,4R,5R,6R)-2-[[(2S)-2-(tert-butoxycarbonylamino)-4-methyl-pentanoyl]amino]-4-(4H-1,2,4-triazol-3-ylsulfanyl)bicyclo[3.1.0]hexane-2,6-dicarboxylate | 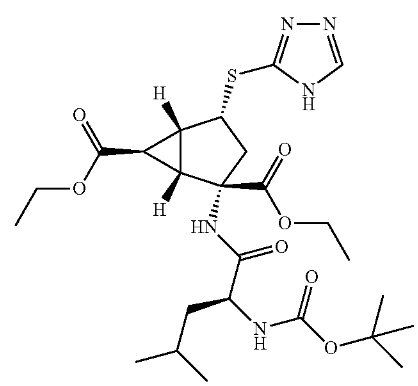 | MS (m/z): 554 (M + 1), 576 (M + 23). |

Preparation 7

(1R,2S,4R,5R,6R)-2-[[(2S)-2-(tert-Butoxycarbonylamino)propanoyl]amino]-4-(4H-1,2,4-triazol-3-ylsulfanyl)bicyclo[3.1.0]hexane-2,6-dicarboxylic acid

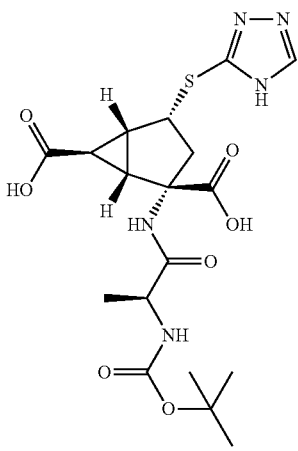

Method 1:

Charge a 2-necked round bottom flask with diethyl (1R,2S,4R,5R,6R)-2-[[(2S)-2-(tert-butoxycarbonylamino)propanoyl]amino]-4-(4H-1,2,4-triazol-3-ylsulfanyl)bicyclo[3.1.0]hexane-2,6-dicarboxylate (195 g, 0.38 mol) and tetrahydrofuran (1.17 L) and cool the mixture to 4° C. using a ice water bath. Add slowly a cold (4° C.) solution of 50% aqueous sodium hydroxide solution (81 mL) in water (1.17 L) over 30 minutes (small exotherm to 8° C.). Remove the ice water bath and stir the mixture at 15° C. After three hours, acidify the mixture to pH=3 using concentrated hydrochloric acid and water (1:3, 500 mL approximately) maintaining the temperature below 20° C. Extract the cloudy solution with ethyl acetate (600 mL then 2×100 mL). Combine the organic layers, wash with brine (100 mL) and discard the aqueous phase. Dry over magnesium sulfate, filter and concentrate to dryness to yield the title compound as a white solid (187 g, 0.41 mol). MS (m/z): 456 (M+1).

Method 2:

Dissolve diethyl (1R,2S,4R,5R,6R)-2-[[(2S)-2-(tert-butoxycarbonylamino)propanoyl]amino]-4-(4H-1,2,4-triazol-3-ylsulfanyl)bicyclo[3.1.0]hexane-2,6-dicarboxylate (319 mg, 0.62 mmol) in tetrahydrofuran (4.2 mL) then add 2M lithium hydroxide (2.5 mL, 5 mmol). Stir the mixture at room temperature overnight. Dilute the reaction mixture with water and wash with ethyl acetate. Discard the organic layer. Adjust the aqueous phase to pH=2 with 1N hydrochloric acid and extract with ethyl acetate. Dry the organic phase through a diatomaceous earth cartridge and concentrate to dryness to give the title compound (244 mg, 86%). MS (m/z): 456 (M+1).

The following compounds are prepared essentially following method 2 of preparation 7.

| Prep No. | Chemical name | Structure | Physical data |
|---|---|---|---|
| 8 | (1R,2S,4R,5R,6R)-2-[[(2S)-2-(tert-Butoxycarbonylamino)-4-methylsulfanyl-butanoyl]amino]-4-(4H-1,2,4-triazol-3-ylsulfanyl)bicyclo[3.1.0]hexane-2,6-dicarboxylic acid | 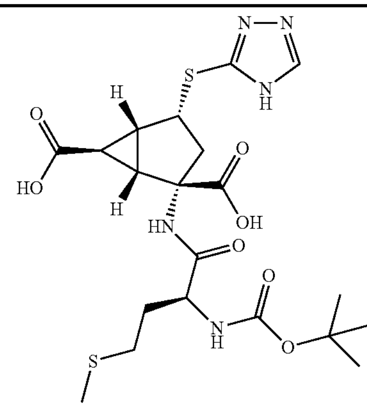 | MS (m/z): 516 (M + 1), 538 (M + 23). |
| 9* | (1R,2S,4R,5R,6R)-2-[[(2S)-2-(tert-Butoxycarbonylamino)-4-methyl-pentanoyl]amino]-4-(4H-1,2,4-triazol-3-ylsulfanyl)bicyclo[3.1.0]hexane-2,6-dicarboxylic acid | 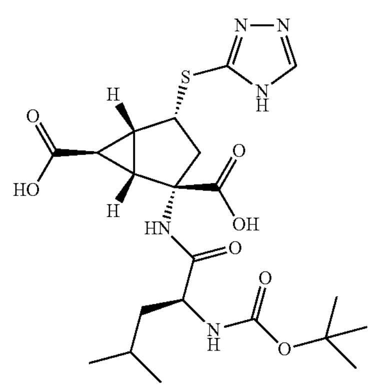 | MS (m/z): 498 (M + 1), 520 (M + 23). |

*The base used is 2.5 M LiOH.

Preparation 10

Diethyl (1R,2S,4R,5R,6R)-2-[[2-(tert-butoxycarbonylamino)acetyl]amino]-4-(4H-1,2,4-triazol-3-ylsulfanyl)bicyclo[3.1.0]hexane-2,6-dicarboxylate

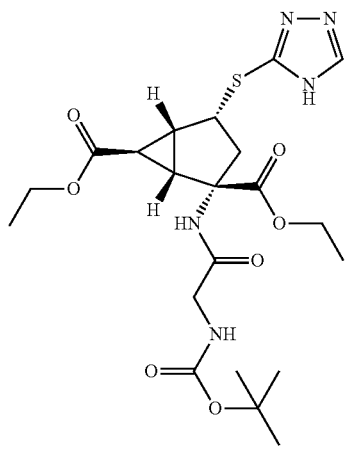

Add thionyl chloride (2.5 mL, 34.32 mmol) to a stirred solution of ditert-butyl (1R,2S,4R,5R,6R)-2-(tert-butoxycarbonylamino)-4-(4H-1,2,4-triazol-3-ylsulfanyl)bicyclo[3.1.0]hexane-2,6-dicarboxylate (2.1 g, 4.23 mmol) in ethanol (40 mL) at 0-5° C. dropwise over 5 minutes with caution (exothermic reaction). Remove the cooling bath and heat the reaction mixture at reflux temperature for 16 hours. Evaporate the volatiles and dry the residue under high vacuum for 7 hours to obtain a colorless foam of diethyl (1R,2S,4R,5R,6R)-2-amino-4-(4H-1,2,4-triazol-3-ylsulfanyl)bicyclo[3.1.0]hexane-2,6-dicarboxylate hydrochloride. Add then 2-(tert-butoxycarbonylamino)acetic acid (0.89 g, 5.07 mmol) and O-(7-azabenzotriazol-1-yl)-N,N,N',N'-tetramethyluronium hexafluorophosphate (1.93 g, 5.07 mmol) to a solution of diethyl (1R,2S,4R,5R,6R)-2-amino-4-(4H-1,2,4-triazol-3-ylsulfanyl)bicyclo[3.1.0]hexane-2,6-dicarboxylate hydrochloride in anhydrous N,N-dimethylformamide (20 mL) at room temperature then add diisopropylethylamine (2 mL, 11.47 mmol) and stir the resulting yellow solution under nitrogen for 18 hours. Concentrate the solvent and partition the residue between ethyl acetate (40 mL) and a saturated solution of sodium hydrogen carbonate in water (40 mL). Stir the mixture for 20 minutes, separate the layers and extract the aqueous layer with more ethyl acetate (40 mL). Combine the organics layers, dry on sodium sulfate and concentrate to dryness. Purify the residue by flash chromatography eluting with ethyl acetate: iso-hexane (80:20 to 100:0) to give the title compound as a colorless solid (2.42 g, 4.86 mmol). MS (m/z): 498 (M+1), 520 (M+23).

Preparation 11

(1R,2S,4R,5R,6R)-2-[[2-(tert-Butoxycarbonylamino)acetyl]amino]-4-(4H-1,2,4-triazol-3-ylsulfanyl)bicyclo[3.1.0]hexane-2,6-dicarboxylic acid

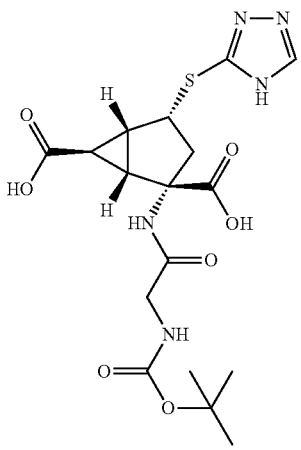

Add 2M sodium hydroxide (4.5 mL, 9 mmol) to a stirred solution of diethyl (1R,2S,4R,5R,6R)-2-[[2-(tert-butoxycarbonylamino)acetyl]amino]-4-(4H-1,2,4-triazol-3-ylsulfanyl)bicyclo[3.1.0]hexane-2,6-dicarboxylate (1.4 g, 2.81 mmol) in tetrahydrofuran (8 mL) at room temperature. Stir the biphasic mixture for 2 hours, dilute the reaction mixture with water (50 mL) and wash with diethyl ether (50 mL). Cool the aqueous layer to 0-5° C., acidify to pH=2 with 2M hydrochloric acid and extract with ethyl acetate (2×60 mL). Combine the organics phases, dry on sodium sulfate and concentrate to give the title compound as a white solid (0.75 g, 1.69 mmol). $^1$H NMR (D$_2$O) δ 1.18-1.27 (m, 1H), 1.32 (s, 9H), 1.44-1.49 (m, 1H), 2.0-2.6 (m, 1H), 2.12-2.19 (m, 1H), 2.65-2.75 (m, 2H), 3.57-3.68 (m, 2H), 4.12-4.21 (m, 1H), 8.23 (s, 1H) as well as some title compound in the remaining aqueous layer (approximately 1.12 mmol). MS (m/z): 442 (M+1), 464 (M+23).

Preparation 12

(1R,2S,4R,5R,6R)-2-Amino-4-(4H-1,2,4-triazol-3-ylsulfanyl)bicyclo[3.1.0]hexane-2,6-dicarboxylic acid hydrochloride

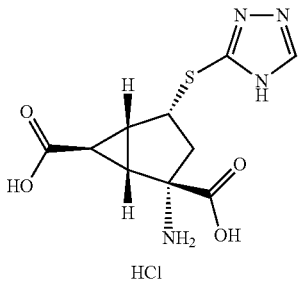

Add 4M hydrogen chloride in 1,4-dioxane (10 mL, 40 mmol) to a solution of ditert-butyl (1R,2S,4R,5R,6R)-2-(tert-butoxycarbonylamino)-4-(4H-1,2,4-triazol-3-ylsulfanyl)bicyclo[3.1.0]hexane-2,6-dicarboxylate (1.97 g, 3.97 mmol) in 1,4-dioxane (10 mL). Heat the mixture to 50° C. with stirring overnight (a white solid starts to precipitate out of solution soon after heating commences). Add ethyl acetate (50 mL) to the reaction mixture (white cloudy solution). Leave the mixture to cool to room temperature then collect the solid by filtration and dry to give a white solid (1.97 g). Dry the solid over the weekend under reduced pressure at 40° C. to give the title compound as a white solid contaminated with some 1,4-dioxane and a small amount of mono tert-butyl ester (1.936 g, 65% purity wt/wt %, 3.95 mmol). MS (m/z): 285 (M+1).

Preparation 13

(1R,2S,5R,6R)-2-(tert-Butoxycarbonylamino)-4-oxo-bicyclo[3.1.0]hexane-2,6-dicarboxylic acid

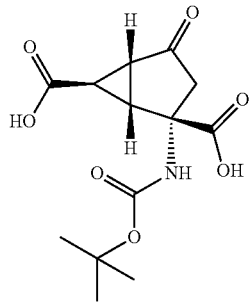

Add 2.5M sodium hydroxide (15.55 mL, 38.88 mmol) to a stirred solution of the ditert-butyl (1S,2S,5R,6R)-2-(tert-butoxycarbonylamino)-4-oxo-bicyclo[3.1.0]hexane-2,6-dicarboxylate (2.0 g, 4.86 mmol) in tetrahydrofuran (24.3 mL) and ethanol (9.72 mL). Heat the reaction mixture to 60° C. and maintain stirring overnight. Continue heating for 4 hours then wash with ethyl acetate. Cool the aqueous phase in an ice bath and acidify to pH=2-3 with 1N hydrochloric acid solution. Extract with ethyl acetate (3 times), dry the organic on sodium sulfate, filter and concentrate to give the title compound as an orange solid (1.4 g, 96%). MS (m/z): 322 (M+23).

Preparation 14

Bis[(2-fluorophenyl)methyl](1S,2S,5R,6R)-2-(tert-butoxycarbonylamino)-4-oxo-bicyclo[3.1.0]hexane-2,6-dicarboxylate

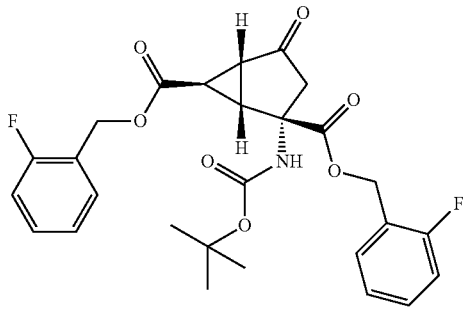

Add 2-fluorobenzyl bromide (0.21 mL, 1.7 mmol) dropwise to a stirred suspension of (1S,2S,5R,6R)-2-(tert-butoxycarbonylamino)-4-oxo-bicyclo[3.1.0]hexane-2,6-dicarboxylic acid (0.17 g, 0.57 mmol) and cesium carbonate (0.37 g, 1.14 mmol) in dry N,N-dimethylformamide (1.42 mL). Stir the resulting mixture at room temperature overnight under nitrogen. Quench with water and dilute with ethyl acetate. Extract the aqueous phase with ethyl acetate (3 times) and wash the organic layers with brine and water. Dry over sodium sulfate, filter and concentrate to give the crude material as a pale brown oil. Purify by flash chromatography eluting with ethyl acetate:hexane (20:80 to 30:70) to give the title compound as a pale yellow oil (229 mg, 79%). MS (m/z): 538 (M+23).

Preparation 15

Bis[(2-fluorophenyl)methyl](1S,2S,4S,5R,6R)-2-(tert-butoxycarbonylamino)-4-hydroxy-bicyclo[3.1.0]hexane-2,6-dicarboxylate

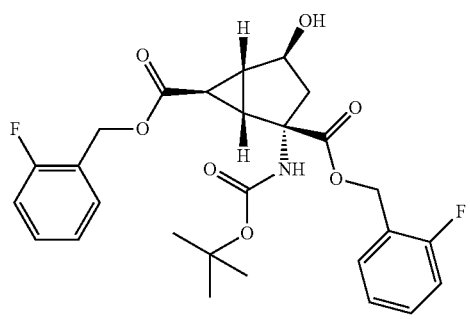

Add 1M L-selectride solution in THF (6.78 mL, 6.78 mmol) dropwise to a stirred solution of bis[(2-fluorophenyl)methyl](1S,2S,5R,6R)-2-(tert-butoxycarbonylamino)-4-oxo-bicyclo[3.1.0]hexane-2,6-dicarboxylate (2.33 g, 4.52 mmol) in tetrahydrofuran (20.3 mL) at −78° C. Stir the resulting orange mixture under nitrogen for 1 hour 45 minutes. Quench with a saturated solution of sodium hydrogen carbonate at −78° C. Dilute with water and ethyl acetate. Separate the layers and wash the organic phase with brine and water. Dry over sodium sulfate, filter and concentrate to dryness to give the crude material as pale yellow oil contaminated with approximately 6% of the minor isomer bis[(2-fluorophenyl)methyl](1S,2S,4R,5R,6R)-2-(tert-butoxycarbonylamino)-4-hydroxy-bicyclo[3.1.0]hexane-2,6-dicarboxylate as detected by MS. Combine the crude material with a second batch similarly prepared from bis[(2-fluorophenyl)methyl](1S,2S,5R,6R)-2-(tert-butoxycarbonylamino)-4-oxo-bicyclo[3.1.0]hexane-2,6-dicarboxylate (0.23 g, 0.44 mmol). Purify the combined material by flash chromatography eluting with ethyl acetate:hexane (20:80 to 50:50) to give the title product as a single isomer (2.49 g, 4.81 mmol). MS (m/z): 540 (M+23).

Preparation 16

Bis[(2-fluorophenyl)methyl](1S,2S,4S,5R,6R)-2-(tert-butoxycarbonylamino)-4-(p-tolylsulfonyloxy)bicyclo[3.1.0]hexane-2,6-dicarboxylate

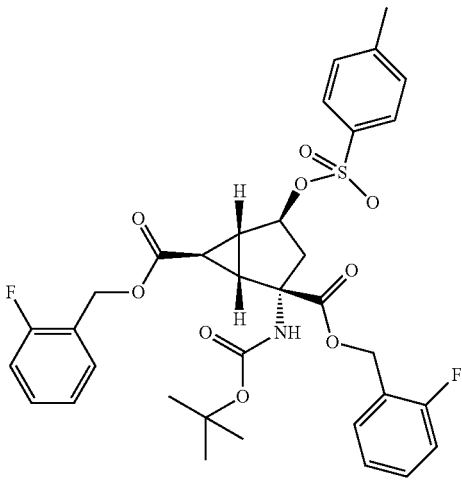

Add p-toluenesulfonyl chloride (1.02 g, 5.31 mmol) to a solution of bis[(2-fluorophenyl)methyl](1S,2S,4S,5R,6R)-2-(tert-butoxycarbonylamino)-4-hydroxy-bicyclo[3.1.0]hexane-2,6-dicarboxylate (2.5 g, 4.83 mmol) in dichloromethane (19.32 mL) at room temperature. Cool into an ice-water bath then add triethylamine (0.74 mL, 5.31 mmol) and N,N-dimethyl 4-aminopyridine portionwise (1 g, 8.21 mmol). Allow to warm to room temperature and maintain stirring overnight under nitrogen. Quench with water and separate the layers. Wash the organic layers with 1M solution of potassium hydrogen sulfate, brine and water. Dry the organic phase over sodium sulfate, filter, concentrate to dryness and dry under vacuum to give a pale yellow foam (2.72 g). Purify by flash chromatography eluting with ethyl acetate:hexane (20:80 to 40:60) to give the title product as a colorless oil (2.7 g, 4.02 mmol). MS (m/z): 672 (M+1).

Preparation 17

Bis[(2-fluorophenyl)methyl](1R,2S,4R,5R,6R)-2-(tert-butoxycarbonylamino)-4-(4H-1,2,4-triazol-3-ylsulfanyl)bicyclo[3.1.0]hexane-2,6-dicarboxylate

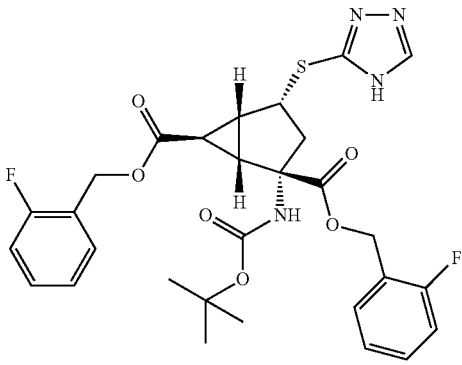

Add 4H-1,2,4-triazole-3-thiol (0.59 g, 5.87 mmol) and potassium carbonate (0.81 g, 5.87 mmol) to a solution of bis[(2-fluorophenyl)methyl](1S,2S,4S,5R,6R)-2-(tert-butoxy carbonylamino)-4-(p-tolylsulfonyloxy)bicyclo[3.1.0]hexane-2,6-dicarboxylate (2.63 g, 3.92 mmol) in dry N,N-dimethylformamide (15.66 mL). Heat the resulting mixture at 70° C. under nitrogen in a sealed tube and maintain stirring overnight. Quench with water and dilute with ethyl acetate. Wash the organic layer with citric acid solution (10% in water), brine. Dry over sodium sulfate, filter and concentrate to give the crude material as a pale brown oil (2.3 g). Purify by flash chromatography eluting with ethyl acetate:hexane (30:70 to 70:30) to give the title product as a colorless oil (1.84 g, 3.06 mmol). MS (m/z): 601 (M+1), 623 (M+23).

EXAMPLE 1

(1R,2S,4R,5R,6R)-2-Amino-4-(4H-1,2,4-triazol-3-ylsulfanyl)bicyclo[3.1.0]hexane-2,6-dicarboxylic acid

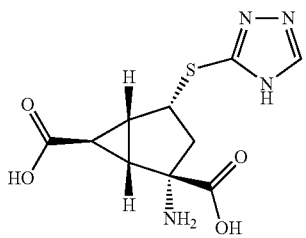

Method 1:

Add 4M hydrogen chloride in 1,4-dioxane (18.42 mL, 7.37 mmol) to a solution of ditert-butyl(1R,2S,4R,5R,6R)-2-(tert-butoxycarbonylamino)-4-(4H-1,2,4-triazol-3-ylsulfanyl)bicyclo[3.1.0]hexane-2,6-dicarboxylate (3.66 g, 7.37 mmol) in 1,4-dioxane, (17.69 mL) and stir the mixture over the weekend at 50° C. Add ethyl acetate and cool the mixture in an ice bath. Collect the white solid by decantation and wash several times with ethyl acetate. Dry the solid in vacuo and purify by ion exchange chromatography. Precondition an ion exchange column (SCX-2 column) with acetonitrile. Dissolve the material in minimum quantity of water and load onto the column. Elute with acetonitrile (2 column volumes), 2N ammonia in methanol:acetonitrile (1:1) (2 column volumes), ammonia in methanol and 7N ammonia in methanol. Concentrate the 2N ammonia in methanol fraction to dryness to give the desired material (1.39 g) as a white solid. Dry the solid for 48 hours at 40° C. to yield the title compound (1.24 g, 66%). $^1$H NMR (D$_2$O) δ 1.41-1.55 (m, 2H), 2.02 (dd, J=3.1 and 6.4 Hz, 1H), 2.15-2.20 (m, 1H), 2.40 (dd, J=8.1 and 14.1 Hz, 1H), 3.22 (s, 1H), 4.20-4.28 (m, 1H), 8.30 (s, 1H).

Method 2:

Dissolve ditert-butyl (1R,2S,4R,5R,6R)-2-(tert-butoxycarbonylamino)-4-(4H-1,2,4-triazol-3-ylsulfanyl)bicyclo[3.1.0]hexane-2,6-dicarboxylate (433 mg, 0.87 mmol) in 1,4-dioxane (7 mL) and add 4M hydrogen chloride in 1,4-dioxane (7 mL, 2.8 mmol). Leave the mixture to shake at 50° C. overnight. Concentrate to dryness. Purify by cationic ion exchange (Dowex Marathon C, Na$^+$ Form strongly acidic). Dissolve the residue in a minimum amount of water to solubilize the material and load onto the resin. Wash the resin successively with 2 column volume of water, then 2 column volume of water:tetrahydrofuran (1:1) and 2 column volumes of water. Elute the desired product with 2 column volumes of 10% pyridine in water. Concentrate to dryness to yield the title compound (202 mg, 82%). MS (m/z): 285 (M+1).

EXAMPLE 2

(1R,2S,4R,5R,6R)-2-[[(2S)-2-Aminopropanoyl]amino]-4-(1H-1,2,4-triazol-3-ylsulfanyl)bicyclo[3.1.0]hexane-2,6-dicarboxylic acid hydrochloride.

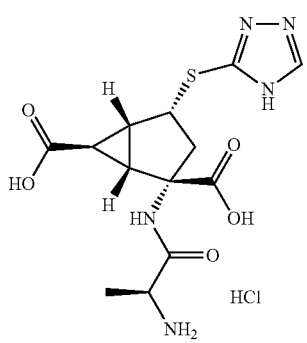

Method 1:

Charge a 5 L 3-necked round bottom flask equipped with a mechanical stirrer with (1R,2S,4R,5R,6R)-2-[[(2S)-2-(tert-butoxycarbonylamino)propanoyl]amino]-4-(4H-1,2,4-triazol-3-ylsulfanyl)bicyclo[3.1.0]hexane-2,6-dicarboxylic acid (186 g, 0.41 mol), in acetone (1.12 L). To this slurry, add 37% hydrochloric acid in water (100 mL) dropwise over 15 minutes. Stir the mixture at 40° C. during one hour. Cool to room temperature and add acetone (3.72 L). Stir the mixture for 2 hours until complete formation of a white gum. Repeat adding acetone (3 L) until formation of a white gum. Remove the acetone, add toluene and concentrate to give an oil. Redissolve the crude in water (400 mL) and freeze-dry the material to yield the title compound as a white solid (143 g; 89%). MS (m/z): 356 (M+1), 378 (M+23). $^1$H NMR (D$_2$O) δ 1.37-1.43 (m, 4H), 1.61 (t, J=3.2 Hz, 1H), 2.31-2.34 (m, 1H), 2.44 (dd, J=2.9 and 6.4 Hz, 1H), 2.77 (dd, J=8.1 and 14.4 Hz, 1H), 3.92 (q, J=7.1 Hz, 1H), 4.20-4.25 (m, 1H), 8.55 (s, 1H).

Method 2:

Dissolve (1R,2S,4R,5R,6R)-2-[[(2S)-2-(tert-butoxycarbonylamino)propanoyl]amino]-4-(4H-1,2,4-triazol-3-ylsulfanyl)bicyclo[3.1.0]hexane-2,6-dicarboxylic acid (244 mg, 0.54 mmol) in ethyl acetate (24.5 mL) and bubble hydrogen chloride gas for 1-2 minutes at 0° C. After 5 minutes at 0° C., shake the reaction at room temperature for 90 minutes. Remove the solvent under vacuum and redissolve the solid in water. Freeze-dry the solution to yield the title compound (180 mg, 86%) as a white solid. MS (m/z): 356 (M+1), 378 (M+23).

EXAMPLE 3

(1R,2S,4R,5R,6R)-2-[[(2S)-2-Amino-4-methylsulfanyl-butanoyl]amino]-4-(4H-1,2,4-triazol-3-ylsulfanyl)bicyclo[3.1.0]hexane-2,6-dicarboxylic acid hydrochloride.

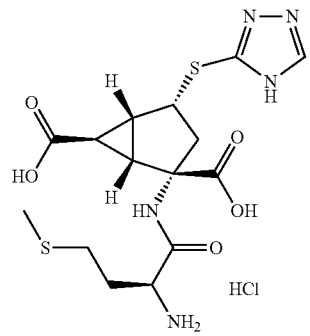

Add 4M hydrogen chloride in 1,4-dioxane (19.35 mL, 77.38 mmol) dropwise to a solution of (1R,2S,4R,5R,6R)-2-[[(2S)-2-(tert-butoxycarbonylamino)-4-methylsulfanyl-butanoyl]amino]-4-(4H-1,2,4-triazol-3-ylsulfanyl)bicyclo[3.1.0]hexane-2,6-dicarboxylic acid (2.66 g, 5.16 mmol) in 1,4-dioxane (26.6 mL) at room temperature in a water bath, and maintain stirring overnight at room temperature. Add methyl-t-butyl ether (200 mL) and stir the mixture for 2 hours. Filter the solid and dry in vacuo overnight. Redissolve the material in water and freeze-dry overnight. Triturate the solid in acetone (10 volumes) at reflux, filter and dry in vacuo under nitrogen for 48 hours to give the title compound (2.33 g, 5.16 mmol) as a white solid. MS (m/z): 416 (M+1).

EXAMPLE 4

(1R,2S,4R,5R,6R)-2-[[(2S)-2-Amino-4-methyl-pentanoyl]amino]-4-(4H-1,2,4-triazol-3-ylsulfanyl)bicyclo[3.1.0]hexane-2,6-dicarboxylic acid hydrochloride

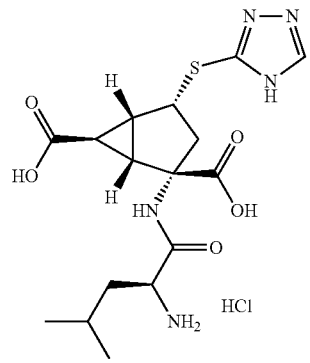

Add 4M hydrogen chloride in 1,4-dioxane (3.01 mL, 12.06 mmol) to a solution of (1R,2S,4R,5R,6R)-2-[[(2S)-2-(tert-butoxycarbonylamino)-4-methyl-pentanoyl]amino]-4-(4H-1,2,4-triazol-3-ylsulfanyl)bicyclo[3.1.0]hexane-2,6-dicarboxylic acid (0.4 g, 0.8 mmol) in 1,4-dioxane (4 mL). Stir the white precipitate appearing immediately after addition overnight. Add methyl-t-butyl ether (16 mL) and collect the white solid by decantation washing several times with methyl-t-butyl ether to give 330 mg of desired material. Combine with a second lot of material prepared similarly from (1R,2R,4S, 5R,6R)-4-[[(2S)-2-(tert-butoxycarbonylamino)-4-methyl-pentanoyl]amino]-2-(4H-1,2,4-triazol-3-ylsulfanyl)bicyclo [3.1.0]hexane-4,6-dicarboxylic acid (100 mg, 0.2 mmol) and 4M hydrogen chloride in 1,4-dioxane (0.75 mL, 3.01 mmol) to give 374 mg of material. Purify half of the material (190 mg) by OASIS® HLB (1 g) cartridge. Acidify the eluent containing the desired material to pH=2-3 with 1N hydrochloric acid and dry under vacuum overnight at 45° C. to yield 170 mg of a white solid. Purify similarly the remaining material and combine to obtain the title compound (290 mg, 0.67 mmol). MS (m/z): 398 (M+1), 795 (2M+1).

EXAMPLE 5

(1R,2S,4R,5R,6R)-2-[(2-Aminoacetyl)amino]-4-(4H-1,2,4-triazol-3-ylsulfanyl)bicyclo[3.1.0]hexane-2,6-dicarboxylic acid hydrochloride

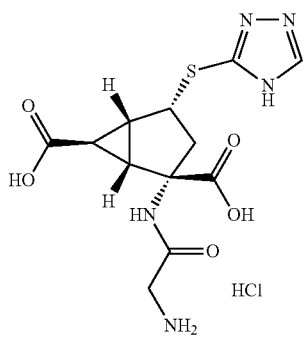

Add 5M hydrochloric acid (10 mL, 50 mmol) to the aqueous solution of ((1R,2S,4R,5R,6R)-2-[[2-(tert butoxycarbonylamino)acetyl]amino]-4-(4H-1,2,4-triazol-3-ylsulfanyl) bicyclo[3.1.0]hexane-2,6-dicarboxylic acid (approximately 1.12 mmol) and stir at room temperature for 5 hours. Concentrate to dryness and purify the residue by cation-exchange chromatography (DOWEX® 50WX8-100). Dissolve the compound in water and adjust to pH=2. Allow the compound to flow through the column at a drip rate of about 1 drop every 1-2 seconds. After the initial loading volume has dropped to the resin surface, rinse with water (5 to 10 mL) and repeat 3 times. Monitor the pH of the effluent and continue rinsing with water until application complete (pH cycle observed: effluent from the column initially at pH=7 then drop to pH=1 and return back to pH=7). Wash the column with at least one column volume each of water, water:tetrahydrofuran (1:1) then water. Displace the product from the resin with 10% pyridine: water. Continue to elute with 10% pyridine: water until no additional product is detected by TLC. Concentrate the fractions containing the product to obtain a colorless solid (173 mg). Dissolve the solid in water (8 mL), add 5M hydrochloric acid (0.11 mL, 0.55 mmol) and freeze-dry the solution for 48 hours to give the title compound as a white solid (195 mg, 0.52 mmol). MS (m/z): 342 (M+1).

EXAMPLE 6

Dibenzyl (1R,2S,4R,5R,6R)-2-amino-4-(4H-1,2,4-triazol-3-ylsulfanyl)bicyclo[3.1.0]hexane-2,6-dicarboxylate

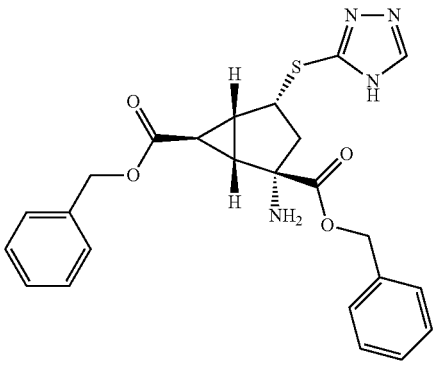

Add acetyl chloride (2.5 mL, 35.14 mmol) to a mixture of benzyl alcohol (18.18 mL, 175.68 mmol) and (1R,2S,4R,5R, 6R)-2-amino-4-(4H-1,2,4-triazol-3-ylsulfanyl)bicyclo [3.1.0]hexane-2,6-dicarboxylic acid hydrochloride (1.61 g, 3.51 mmol) at room temperature. Heat the cloudy reaction mixture at 60° C. under nitrogen. After 3 days, cool to room temperature, dilute the reaction mixture carefully with acetonitrile (10 mL) and purify by SCX-2 column (20 g). Load the reaction mixture onto a column pre-conditioned with acetonitrile, wash with acetonitrile (×2) then elute with 2N ammonia solution in methanol: acetonitrile (2 column volumes) then evaporate the solvent in vacuo to give a white gum (576 mg) consistent with the desired crude product. Elute then with 7N ammonia in methanol (1 column volume) and remove the solvent in vacuo to give a white solid consistent with (1R,2S, 4R,5R,6R)-2-amino-6-benzyloxycarbonyl-4-(4H-1,2,4-triazol-3-ylsulfanyl)bicyclo[3.1.0]hexane-2-carboxylic acid (750 mg). MS (m/z): 372 (M+1). Purify the crude product by flash chromatography eluting with ethyl acetate:cyclohexane (60:40 to 100:0) twice to give the title compound as a white solid (430 mg). Dissolve in a mixture of dichloromethane: ethyl acetate: acetonitrile, concentrate to dryness and dry under high vacuum at room temperature overnight to give the title compound as a white solid (402 mg, 25%). MS (m/z): 465 (M+1)

Obtain a second batch of title compound similarly by adding acetyl chloride (998 µL, 14.02 mmol) to a mixture of benzyl alcohol (7.26 mL, 70.11 mmol) at room temperature and (1R,2S,4R,5R,6R)-2-amino-6-benzyloxycarbonyl-4-(4H-1,2,4-triazol-3-ylsulfanyl)bicyclo[3.1.0]hexane-2-carboxylic acid (0.75 g, 1.40 mmol). Heat the reaction at 60° C. under nitrogen. After 3.5 days add with caution thionyl chloride (204.31 µL, 2.8 mmol) to the reaction mixture and maintain heating for 24 hours. Cool the reaction to room temperature and dilute with acetonitrile (10 mL). Purify by SCX-2 column (20 g) to give a white solid (567 mg). Purify the crude product by flash chromatography eluting with ethyl acetate: cyclohexane (60:40 to 100:0). Purify further by flash chromatography eluting with ethyl acetate:cyclohexane (60:40 to 80:20) to give after drying a further batch of the title compound (140 mg, 21%). MS (m/z): 465 (M+1).

EXAMPLE 7

Bis[(2-fluorophenyl)methyl](1R,2S,4R,5R,6R)-2-amino-4-(4H-1,2,4-triazol-3-ylsulfanyl)bicyclo[3.1.0]hexane-2,6-dicarboxylate hydrochloride

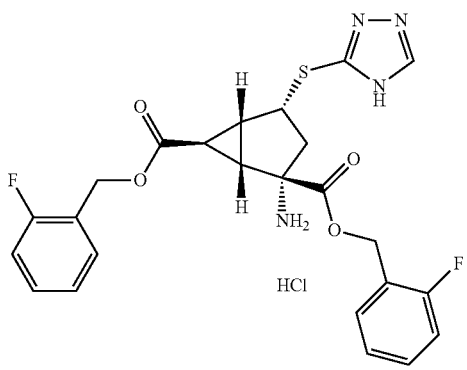

Add a solution of concentrated hydrogen chloride in ethyl acetate (7.91 mL) to a solution of bis[(2-fluorophenyl)methyl](1R,2S,4R,5R,6R)-2-(tert-butoxycarbonylamino)-4-(4H-1,2,4-triazol-3-ylsulfanyl)bicyclo[3.1.0]hexane-2,6-dicarboxylate (0.48 g, 0.79 mmol) in ethyl acetate (7.91 mL). Stir the resulting mixture at room temperature overnight. Remove the hydrogen chloride by bubbling nitrogen through the reaction mixture. Concentrate and dry the resulting colorless oil in the vacuum oven at 40° C. overnight. Redissolve the material in water, keep in the freezer for 48 hours and freeze-dry to give the title compound (379 mg, 89%). MS (m/z): 501 (M+1), 523 (M+23).

EXAMPLE 8

Bicyclo[3.1.0]hexane-2,6-dicarboxylic acid, 2-[[(2S)-2-amino-1-oxopropyl]amino]-4-(4H-1,2,4-triazol-3-ylthio)-, monoammonium salt, (1R,2S,4R,5R,6R)—, monohydrate

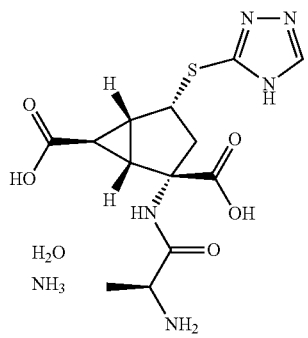

To purified water (28.0 kg) is added (1R,2S,4R,5R,6R)-2-[[(2S)-2-(tert-butoxycarbonylamino)propanoyl]amino]-4-(4H-1,2,4-triazol-3-ylsulfanyl)bicyclo[3.1.0]hexane-2,6-dicarboxylic acid (11.05 kg) with stirring. Add hydrochloric acid (5N, 8.5 kg) to the mixture with temperature below 50° C. Heat the mixture at 50° C.-55° C. for 1.5-2.0 hours. Cool the mixture to 15° C.-25° C. Adjust pH to 9 by adding ammonium hydroxide (25%, 4.8 kg) dropwise and maintaining temperature at 45° C.-50° C. Then add ethanol (34 kg) and cool to 20° C.-25° C. In a separate vessel, charge purified water (6.5 kg), polish filtered absolute ethanol (45 kg of) and seed crystal of bicyclo[3.1.0]hexane-2,6-dicarboxylic acid, 2-[[(2S)-2-amino-1-oxopropyl]amino]-4-(4H-1,2,4-triazol-3-ylthio)-, monoammonium salt, (1R,2S,4R,5R,6R)—, monohydrate prepared separately (0.1 kg). Heat this mixture to 45° C.-50° C., then add the ammonium hydroxide (polish filtered) reaction solution dropwise. Heat the mixture at 50° C.-55° C. for 2-3 hours and add absolute ethanol (72 kg) dropwise and maintain temperature at 50° C.-55° C. Bring the reaction mixture temperature to 40° C.-45° C. under a nitrogen blanket for 1-1.5 hours. Cool mixture to 30° C.-35° C. and maintain at this temperature for 1-1.5 hours. Cool mixture to 20° C.-25° C. and maintain at this temperature for 3-4 hours still under a nitrogen blanket. Filter the precipitates and rinse cake with purified water/ethanol (1:10). Dry the cake under vacuum at 50° C.-55° C. to give the title compound as a white solid (6.82 kg). MS (m/z): 391 (M+1)

X-ray powder diffraction (XRD) patterns of crystalline solids are obtained on a Bruker D4 Endeavor X-ray powder diffractometer, equipped with a CuKα source (λ=1.54060 Å) and a Vantec detector, operating at 35 kV and 50 mA. The sample is scanned between 4° and 40° in 2θ, with a step size of 0.009° in 2θ. The dry powder is packed on a quartz sample holder and a smooth surface is obtained using a glass slide. The crystal form diffraction patterns are collected at ambient temperature and relative humidity. In the present case, a peak position variability of ±0.2 in 2θ takes into account potential variations without hindering the unequivocal identification of the indicated crystal form. Confirmation of a crystal form may be made based on any unique combination of distinguishing peaks (in units of °2θ), typically the more prominent peaks. The crystal form diffraction patterns, collected at ambient temperature and relative humidity, are adjusted based on NIST 675 standard peaks at 8.85 and 26.77 degrees 2-theta.

Thus, a sample crystalline form of the compound is characterized by an XRD pattern using CuKα radiation as having diffraction peaks (2θ values) as described in Table 1 below, and in particular having peaks at 18.61 in combination with one or more of the peaks selected from the group consisting of 21.07, 15.34, 14.74, and 19.20; with a tolerance for the diffraction angles of 0.2 degrees.

TABLE 1

X-ray powder diffraction peaks of Example 8.

| 2θ (°) | Relative Intensity (%) |
| --- | --- |
| 7.34 | 6 |
| 9.25 | 9 |
| 10.88 | 5 |
| 11.44 | 6 |
| 12.35 | 6 |
| 14.74 | 24 |
| 15.05 | 8 |
| 15.34 | 25 |
| 16.39 | 12 |
| 17.35 | 12 |
| 18.07 | 18 |
| 18.29 | 19 |
| 18.61 | 100 |
| 19.20 | 38 |
| 19.47 | 16 |
| 20.27 | 8 |
| 20.88 | 36 |
| 21.07 | 55 |

TABLE 1-continued

X-ray powder diffraction peaks of Example 8.

| 2θ (°) | Relative Intensity (%) |
|---|---|
| 21.91 | 36 |
| 22.22 | 11 |
| 22.69 | 40 |
| 23.06 | 23 |
| 24.03 | 14 |
| 24.55 | 29 |
| 26.06 | 10 |
| 26.46 | 16 |
| 27.42 | 23 |
| 28.08 | 22 |
| 29.01 | 11 |
| 29.31 | 7 |
| 30.04 | 14 |
| 30.89 | 10 |
| 32.30 | 11 |
| 34.87 | 13 |
| 35.59 | 14 |

The mGlu receptors are G-protein-coupled receptors that modulate neuronal excitability. More particularly, altered glutamate neurotransmission has been linked to schizophrenia, but all commonly prescribed antipsychotics act on dopamine receptors. Various studies support Group II mGlu receptor (which includes mGlu2 and/or mGlu3) activation for the treatment of schizophrenia. In particular, recent data demonstrate that a mGlu 2/3 receptor agonist has antipsychotic properties and may provide a new alternative for the treatment of schizophrenia (Patil et al., *Nature Medicine* (2007) 13(3), 1102-1107). Studies demonstrate that the antipsychotic activity of mGlu2/3 agonists are mGlu2 mediated. Studies also demonstrate that mGlu2/3 agonists have anxiolytic, antidepressant and neuroprotective properties. Therefore, mGlu2 agonists may be useful in the treatment of psychiatric disorders, such as bipolar disorder, schizophrenia, depression, and generalized anxiety disorder.

Since the compounds of the present invention are mGlu2 agonists, they may be suitable for treating the aforementioned disorders.

Human mGlu2 Agonist FLIPR Assay

AV-12 cell lines, derived from Syrian Hamster fibroblasts and stably expressing the human mGlu2 receptor and co-transfected with the rat glutamate transporter EAAT 1 (Excitatory Amino Acid Transporter 1) and the Gα15 subunit, are used for these studies. The expression of Gα15 allows Gi-coupled receptors to signal through the phospholipase C pathway, resulting in the ability to measure receptor activation by a fluorometric calcium response assay. The cell lines are maintained by culturing in Dulbecco's Modified Eagle's Medium (DMEM) with high glucose and pyridoxine hydrochloride supplemented with 5% dialyzed fetal bovine serum, 1 mM sodium pyruvate, 10 mM HEPES (4-(2-hydroxyethyl)-1-piperazineethanesulfonic acid), 1 mM of L-glutamine, and 5 μg/mL blasticidin (all media are purchased from Invitrogen). Confluent cultures are passaged biweekly using an enzyme-free dissociation solution (Chemicon S-004-B). Cells are harvested 24 hours prior to assay and dispensed using a Matrix Well-Mate cell seeder at 85,000 (mGlu2) or 115,000 (mGlu3) cells per well into 96-well, black-walled, poly-D-lysine-coated plates (BD BioCoat #354640) in medium containing only 250 (mGlu2) or 125 (mGlu3) μM L-glutamine (freshly added).

Intracellular calcium levels are monitored before and after the addition of compounds using a Fluorometric Imaging Plate Reader (FLIPR, Molecular Devices). The assay buffer is comprised of Hank's Buffered Salt Solution (HBSS; Sigma) supplemented with 20 mM HEPES. The medium is removed and the cells are incubated with 8 μM Fluo-3AM (Molecular Probes, F-1241; 50 μL per well) in assay buffer for 90 minutes at 25° C. The dye solution is removed and replaced with fresh assay buffer (50 μL per well). A single-addition FLIPR assay generating an 11-point concentration response curve (3× dilutions starting at 10 μM) for the agonist glutamate (Fisher A125-100) is conducted prior to each experiment to confirm the typical $EC_{50}$ response. Results are analyzed using Prism v4.03 (GraphPad Software). Compounds of the present invention are tested in a single-addition FLIPR assay using a 10-point concentration response profile using 3× dilutions starting at a final concentration of 25 μM. Compounds of the present invention are solubilized as 10 mM stocks in 0.1N NaOH and stored at −20 C. They are diluted through a three-fold dilution series into assay buffer. After taking an initial 5-sec fluorescent read on the FLIPR instrument, a compound of the present invention is added to the cell plate (50 μL per well). Data are collected every second for the first 30 seconds and then every 3 seconds for a total of 90 seconds in order to detect agonist activity. The maximal response is defined as that induced by ECmax (100 μM glutamate). The compound effect is measured as maximal minus minimal peak heights in relative fluorescent units (RFUs) corrected for basal fluorescence measured in the absence of glutamate. Determinations are carried out using single plates. Agonist effects are quantified as percent stimulation induced by compound alone relative to the maximal glutamate response. All data are calculated as relative $EC_{50}$ values using a four-parameter logistic curve fitting program (ActivityBase v5.3.1.22).

The compound of Example 1 was measured in the hmGlu2 FLIPR assay run substantially as above to have an $EC_{50}$ of 23.0 nM±3.9 (n=5, error calculated as SEM). This result demonstrates that Example 1, the active compound for Examples 2 through 8, is an mGlu2 agonist. Compound 1SR, 2RS,4SR,5SR,6SR-2-amino-4-(phenylthio)-bicyclo[3.1.0] hexane-2,6-dicarboxylic acid, as described in WO9717952, measured in the hmGlu2 FLIPR assay run substantially as above had an $EC_{50}$ of >25,000 nM.

Reversal of Phencyclidine (PCP)-Induced Hyperlocomotor Activity in Rats

Administration of NMDA receptor antagonists, such as ketamine or phencyclidine (PCP), produces psychotomimetic-like effects in humans that are similar to those symptoms observed in patients with schizophrenia. The ability of agents to reverse the locomotor-stimulating effects of NMDA antagonists are often used as an animal model of psychosis, demonstrating good predictive validity for detecting clinical efficacy of medications for schizophrenia and bipolar disorder.

Motor activity is monitored by placing individual male, Sprague-Dawley (Harlan, Indianapolis, Ind.) rats in transparent, plastic shoe-box cages of the dimensions 45×25×20 cm, with 1 cm depth of wood chips as bedding, and a metal grill on top of the cage. Motor monitors (Kinder Scientific) consist of a rectangular rack of 12 photobeams arranged in an 8×4 formation, (or a high density grouping of 22 in a 15×7 pattern) at a height of 5 cm, with a second rack (for measuring rearing behaviors) at a height of 15 cm. The shoe box cage is placed inside of these racks, with the racks on a 3 foot high tabletop in an isolated room. A compound of the present invention is dosed (intraperitoneal route (i.p.), non-prodrug) within a range of 0.3-10 mg/kg, 30 minutes prior to a 5 mg/kg challenge dose of phencyclidine (PCP). A compound of the present invention is dosed (oral route, prodrug) within a range of 0.3-30 mg/kg, in overnight fasted rats, 4 hours prior to a 5 mg/kg challenge dose of PCP. On the test day, rats are placed in the test cage and allowed to acclimate for 30 minutes prior to PCP challenge; rats are monitored for an additional 60 minutes following PCP administration.

Data analysis and $ED_{50}$ calculations are conducted using GraphPad Prism (San Diego, Calif. USA). Power analyses have determined that 8-10 rats per group are needed to have appropriate statistical power for detecting treatment differences (power=0.8). A one-way analysis of variance (ANOVA) with a post-hoc Dunnett's multiple comparison test is conducted on the total 60 minute locomotor activity. $ED_{50}$ calculations are performed using non-linear regression curve fitting on percent reversal transformed data for each dose.

The compound of Example 1 was measured in this assay run substantially as above to have an $ED_{50}$ of 1.23 mg/kg (i.p.). The compounds of Examples 2 and 3 were measured in this assay run substantially as above to have an $ED_{50}$ of 2.94 mg/kg (p.o.) and 5.46 mg/kg (p.o.), respectively. These results demonstrate that compounds within the scope of the present invention are useful medications for schizophrenia and bipolar disorder.

Reversal of Phencyclidine (PCP)-Induced Hyperlocomotor Activity in Mice

This assay for Reversal of Phencyclidine (PCP)-Induced Hyperlocomotor Activity in Mice is run substantially as the Reversal of Phencyclidine (PCP)-Induced Hyperlocomotor Activity in Rats assay provided above, using mice instead of rats and with the changes noted below.

Motor activity is monitored by placing individual male, ICR(CD-1), (Harlan, Indianapolis, Ind.) mice in transparent, plastic shoe-box cages of the dimensions 45×25×20 cm, with 0.5 cm depth of wood chips as bedding, and plastic lid on top of the cage. Motor monitors (Kinder Scientific) consist of a rectangular rack of 12 photobeams arranged in an 8×4 formation, (or a high density grouping of 22 in a 15×7 pattern) at a height of 2.5 cm. The shoe box cage is placed inside of these racks, with the racks on a 3 foot high tabletop in an isolated room. A compound of the present invention is dosed (intraperitoneal route, non-prodrug) usually within a range of 0.3-30 mg/kg; though higher doses may be used, 30 minutes prior to a 7.5 mg/kg challenge dose of phencyclidine (PCP). On the test day, mice are placed in the test cage and allowed to acclimate for 45 minutes prior to PCP challenge; mice are monitored for an additional 60 minutes following PCP administration.

Power analyses have determined that 7-8 mice per group are needed to have appropriate statistical power for detecting treatment differences (power=0.8).

In a single dose experiment of 10 mg/kg, the compound of Example 1 was measured in this assay run substantially as above to produce 78±9% inhibition of PCP evoked ambulations (i.p.). In a multiple dose experiment, the compound of Example 1 was measured in this assay run substantially as above to produce 81±5% inhibition of PCP evoked ambulations (i.p.) at a 10 mg/kg dose. These results demonstrate that compounds within the scope of the present invention are useful medications for schizophrenia and bipolar disorder. Compound 1SR,2RS,4SR,5SR,6SR-2-amino-4-(phenylthio)-bicyclo[3.1.0]hexane-2,6-dicarboxylic acid measured in the assay run substantially as above produced 18±11% inhibition of PCP evoked ambulations (i.p.) in a single dose experiment of 10 mg/kg, 5±10% inhibition of PCP evoked ambulations (i.p.) in a multiple dose experiment for the 10 mg/kg dose, and 19±8% inhibition of PCP evoked ambulations (i.p.) in a multiple dose experiment for the 100 mg/kg dose.

Attenuation of Stress-Induced Hyperthermia in Rats

Hyperthermia, a rise in core body temperature, is a general phenomenon that has been reliably demonstrated in many mammals, including humans, in response to stress. In many anxiety disorders, hyperthermia occurs as part of the pathology and is considered a symptom of the disease. Compounds which attenuate stress-induced hyperthermia in animals are believed to be useful in treating anxiety disorders in humans. Generalized anxiety disorder is an example of such disorders that may be treated with such compounds. The conventional and minimally-invasive method for analyzing stress-induced hyperthermia is by measuring body temperature, and stress-induced increases in body temperature, via rectal thermometer. Male Fischer F-344 rats (Harlan, Indianapolis, Ind., USA) weighing between 275-350 g are tested. All animals are individually-housed with food and automated water available ad libitum, and maintained on a 12 h light/dark cycle (lights on at 06:00). Animals are fasted for approximately 12-18 hours before the experiment, which is conducted during the light phase. Rats are dosed two hours prior to the experiment by either intraperitoneal (i.p., non-prodrug) or per os (p.o., prodrug) route of administration in a dose volume of 1 mL/kg. Compounds of the present invention were dosed at 0.3, 1, 3, and 10, mg/kg (i.p.) and 4.13, 13.78, and 41.35 mg/kg (p.o.). These oral doses correspond to doses of the active drug substance of 3, 10 and 30 mg/kg, respectively. The vehicle used in these studies is saline with enough NaOH added to achieve a pH between 5-7. The mGluR5 antagonist MTEP (3-[(2-methyl-1,3-thiazol-4-yl)ethynyl]pyridine), which has demonstrated robust anxiolytic-like activity in preclinical models, is used as a comparator (5 mg/kg, i.p. route, dissolved in water). Immediately following dosing, rats are returned to their home cage, and the experimenter turns off the lights and leaves the room. The dosing room is darkened for the remainder of the 1-hr pretreatment period.

After the pretreatment period, rats are taken individually to a brightly lit adjacent room where baseline body temperatures are determined by insertion of a rectal probe lubricated with mineral oil. Body temperature is assessed using a PHYSITEMP BAT-12® Microprobe Thermometer with a PHYSITEMP RET-2® rat rectal probe (Physitemp Instruments Inc., Clifton, N.J., USA). The probe is inserted approximately 2 cm into the rectum, to measure the core body temperature (this is the baseline body temperature, T1, in degrees Celsius). Ten minutes later a second body temperature measurement is recorded (T2). The difference in body temperature (T2−T1) is defined as the stress-induced hyperthermic response. The dose at which a compound of the present invention produces a 35% reduction in stress-induced hyperthermic response, relative to the vehicle response, is defined as the $T_{35}$ dose.

The compound of Example 1 was measured in this assay run substantially as above to have a $T_{35}$ of 1.27 mg/kg (i.p.). The compound of Example 2 was measured in this assay run substantially as above to have a $T_{35}$ of 16.2 mg/kg (p.o.). These results demonstrate that compounds within the scope of the present invention are useful medications for anxiety disorders. More particularly, compounds within the scope of the present invention may be useful medications for generalized anxiety disorder.

Forced Swim Test in Rodents

The rodent forced swim test assay is well characterized and displays good predictive validity for detecting antidepressant-like activity of current medications for major depressive disorder. In this assay, mechanisms with purported antidepressant-like activity decrease immobility in a brief inescapable forced swim episode.

The forced-swim test is conducted with both mice (male, NIH-Swiss mice, 20-25 g, Harlan Sprague-Dawley, Indianapolis, Ind.) and rats (male, Sprague-Dawley rats, 250-350 g, Harlan Sprague-Dawley, Indianapolis, Ind.). Mice are placed in clear plastic cylinders (diameter 10 cm; height: 25 cm) filled to 6 cm with 22-25° C. water for six min. The duration of immobility is recorded during the last 4 min of a six-minute trial. Rats are treated similarly, albeit in clear plastic cylinders of larger dimensions (diameter: 18 cm; height: 40 cm) filled with water (22-25° C.) to a depth of 16 cm for 15 min. Additionally, mice receive a single forced swim exposure; rats receive two, 5-min sessions separated by 24 hours (data is recorded only on Day 2). The compound of Example 1 is tested in mice using intraperitoneal dosing (1, 3, or 10 mg/kg), 60 min prior to testing. The compound of Example 2 is tested in rats following oral dosing (1.4, 4.1, or 13.8 mg/kg; corresponds to 1, 3, or 10 mg/kg of active equivalent). Example 2 is administered 5 min following the first forced swim exposure and 120 min prior to the test session on Day 2. Imipramine is used as a positive control for these studies. Compounds are formulated in a water vehicle, with minimal NaOH being added to Example 1 and Example 2. Compounds are in a clear solution. The amount of time spent immobile (defined as movements only necessary to keep the subject's head above water) is the dependent measure and recorded by an observer blinded to the drug treatment of the subjects. Data are analyzed by post-hoc Dunnett's test with alpha level set at 0.05. The mouse version of the forced swim test is most commonly used. An $ED_{60}$ value (60% of the amount of immobility relative to vehicle controls) is calculated to estimate potency of the test compounds. Under these test conditions, rats do not respond as robustly as do mice and statistical significance and maximal efficacy relative to the positive control imipramine are used to evaluate treatment response.

Example 1 was measured in this assay run substantially as above and produced prominent antidepressant-like effects in mice ($F_{4,39}$=9.9, p<0.0001). The $ED_{60}$ is 10.5 mg/kg and the maximal effect is a 61% of vehicle immobility levels at the 10 mg/kg dose relative to vehicle control levels. In four separate replications of this study the mean (+standard error of the mean) $ED_{60}$ is 6.1±2.5 mg/kg and the maximal effect is 49.5±11.5% of vehicle-treated immobility levels. In comparison, the effect of the antidepressant imipramine over multiple studies is 8.6±1.2 mg/kg ($ED_{60}$) and 39±1.2% of vehicle immobility levels. In rats, Example 2 was measured in this assay run substantially as above and significantly decreased immobility time [F(4,29)=14.72, p<0.0001] following dosing with 4.1 and 13.8 mg/kg. The maximal effect of Example 2 reduces immobility to 68% of vehicle-treated rats. By comparison, 30 mg/kg imipramine reduces immobility to 70% of vehicle controls. These results demonstrate that compounds within the scope of the present invention are useful medications for depression.

In Vitro PepT1 GlySar Inhibition Screen and $IC_{50}$ Determination

PepT1 assays are established to examine the ability of the amino acid prodrug compounds to interact with the intestinal absorption transporter PepT1.

HeLa cells, derived from human intestine, (American Type Culture Collection) are grown in Hyclone Medium (Invitrogen, Cat# SH30243) containing 10% fetal bovine serum (FBS), 0.1 mM non essential amino acids (NEAA), and 100 units/mL penicillin with 100 µg/mL streptomycin at 37° C. in a 5% $CO_2$ humidified atmosphere. The cell line is used for up to 40 passages and then discarded. Frozen cells in 1 ml vials are thawed in water bath for 1-2 minutes and added to 5 mL of cell medium at 37° C. Each of the T-flasks is provided with 8.5 mL of the fresh medium and 1.5 mL of the cell stock. Cells are passaged twice during a week. This is achieved by rinsing the flasks with 10 mL of phosphate buffered saline-ethylene diaminetetra acetic acid (PBS-EDTA), adding 2 mL of trypsin for 2-5 minutes, to detach the cells, and adding 8 mL of fresh medium to inhibit further activity of trypsin. Each new flask receives a combination of 8.5 mL of fresh medium and 1.5 mL of cell stock, in order to obtain 1:6 cell dilution. Cells are incubated at 37° C., until ready for the uptake study.

Cells that are 70-80% confluent in the T-flasks are plated 1 day prior to the transfection procedure. The flask with the cell stock is treated with PBS-EDTA and trypsin to detach the cells, and transfection medium is used from this point. Transfection medium consists of Dulbecco's Modified Eagle Medium (DMEM)+NEAA. To each well, 0.5 mL of the cell mixture is added ($1.3 \times 10^5$ is the desired cell concentration) and the cells are incubated at 37° C. overnight. Twenty four hours before the assay, cells are transfected with PEPT1. Transfection mixture is prepared by mixing 600 µL of serum free transfection medium, 18 µL of FuGene6 (Roche Diagnostics), and 11 µg of the PepT1 DNA. The transfection reagent-DNA complex is incubated for 20 minutes and 24 µL of the reagent-DNA complex is added to each well.

Inhibition of PEPT1-mediated [glycyl-1-2-$^{14}$C]Glyclysarcosine (GlySar) uptake activity is measured in the cells cultured in the 24-well plates 24-hours post transfection as previously published (Zhang et al. 2004. J. Pharm. Exper Ther. 310:437-445). To measure the ability of a compound of the present invention to inhibit the uptake of [$^{14}$C]Gly-Sar, prodrug compounds are incubated with 80 to 90% confluent PepT1 transiently transfected HeLa cells at 5 mM in pH 6.0 uptake medium in the presence of 5 µM [$^{14}$C]Gly-Sar (Moravek Biochemicals) and 20 µM cold Gly-Sar. Uptake media consists of 140 mM NaCl, 5.4 mM KCl, 1.8 mM $CaCl_2$, 0.8 mM $MgSO_4$, 5 mM Glucose, 25 mM tris(hydroxymethyl)aminomethane buffer (TRIS). The solution is then brought to pH 6.0 using 2-(N-morpholino)ethanesulfonic acid. The incubation volume is 500 µL and is performed at room temperature for 3 minutes. To stop the uptake at the conclusion of the incubation time, the uptake media is aspirated off of the cell monolayer and 500 µL of ice cold PBS added to the well. The cells are washed 3 times with 500 µL of room temperature PBS without $Ca^{+2}$ and $Mg^{+2}$. The cells are then lysed with 300 µL of 1% Triton X100 $H_2O$ solution. A 200 µL aliquot is removed and radioactivity is determined by liquid scintillation counting to measure the [$^{14}$C]Gly-Sar present in each of the incubation wells. A no inhibitor control is established and the percent inhibition of each prodrug is calculated with respect to this control. A negative control (Glycine) and two positive controls (Cefadroxil and Cefalexin) are performed in parallel with each experiment to demonstrate viability of the assay system. Prodrug compounds with GlySar uptake inhibition equal or better than Cephalexin are considered acceptable. Mean values±standard deviation are 10.1±9.5% (n=19) for Glycine, 53.2±13.2% (n=19) for Cefadroxil, and 37.5±14.7% (n=18) for Cephalexin.

For the PepT $IC_{50}$ assay, prodrug compounds are incubated at a range of concentrations (0.0625 to 25 mM) in the presence of 5 μM [$^{14}$C]Gly-Sar and 20 μM cold Gly-Sar. The incubation and sampling procedures are exactly the same as the PepT1 screen described above. [$^{14}$C]Gly-Sar uptake data are evaluated for each of the prodrug compound concentrations and $IC_{50}$ values are calculated.

The compounds of Examples 2, 3, 4, and 5 were measured in this assay run substantially as above to have hPepT1 [3H]Gly-Sar uptake inhibition at 5 mM of 38% (n=3, SD=18.4), 51% (n=1), 32% (n=1), and 44% (n=1), respectively. The compounds of Examples 2 and 3 were measured in this assay run substantially as above to have hPepT1 [3H]Gly-Sar uptake inhibition $IC_{50}$ of 1.84 mM (SE=0.42) and 5.36 mM (SE=1.69), respectively. These results demonstrate that amino acid prodrug compounds within the scope of the present invention are orally absorbed via the PepT1 transporter.

In Vitro Intestinal Prodrug Hydrolysis Assay

Frozen human duodenum intestinal homogenates (1:2 tissue:buffer ratio using 100 mM Tris Phosphate buffer, pH 7.4) are obtained from Celsius In Vitro Technologies (Baltimore, Md.) that were both phenylmethylsulphonylfluoride (PMSF) and EDTA free.

Each lot of human duodenum is obtained from a single donor and the intestine is scraped and the sections are frozen separate. All original tissue collections are performed at 4° C. and immediately frozen at −70° C. Human intestinal homogenates are thawed and diluted to a final protein concentration of 0.5 mg/mL in 100 mM PBS buffer, pH 7.4 immediately prior to the incubations.

Incubations are conducted in 96-well plates and all prodrug compounds are run in duplicate on each day. Stock prodrug compound solutions are prepared in water at a concentration of 1 mM. A 200 μL aliquot of 0.5 mg/mL intestinal homogenate and 196 μL of 100 mM PBS buffer are placed in a 96-well plate in a 37° C. water bath. Using a 96-well pipettor, 4 μL of the 1 mM prodrug compound solution is transferred into the homogenate. Immediately after addition of the prodrug compound (time zero) and after 1 hour incubation, 50 μL samples of the incubation mixture are removed using an automated disposable simultaneous 96 well pipettor and added directly to 200 μL of methanol quench solution containing 100 ng/mL of Internal Standard. The samples are then centrifuged at 3500 rpm for 5 minutes at 10° C. The supernatant (200 μL) is transferred to a final 96 well PCR plate and sealed for analysis by LC/MS/MS.

Concentrations of hydrolyzed compounds of the present invention in the incubation mixtures are determined using LC/MS/MS detection on a Sciex API 4000 quadrapole mass spectrometer with Analyst version 1.4.2, TurboIonSpray, positive ionization, and Selected Reaction Monitoring (SRM). A Waters Atlantis® T3 (20×2.1 mm, 5 μM) HPLC column is used at ambient temperature with a flow rate of 1.0 mL/min and a mobile phase gradient from 0.1% mobile phase A to 99% mobile phase A. Mobile phase A is 1000:5 water:heptafluorobuteric acid and mobile phase B is 1:1 methanol:glacial acetic acid.

Concentrations of hydrolyzed compounds of the present invention in the intestinal incubation mixtures are determined from standard curves prepared by replicate two-fold dilution starting at 10 μM in 100 mM PBS pH 7.4 and subsequently quenched with methanol-internal standard solution identical to the samples. Averages and standard deviations are calculated using Microsoft® Office Excel® 2007. Amount of hydrolysis is determined as a molar percentage of compound formed relative to prodrug compound concentration added. Hydrolysis of the positive control, Internal Prodrug Compound A to Internal Compound Drug A, run in every batch averaged 75.3% (n=20). Final values are then normalized relative to the formation of Internal Compound Drug A.

The compounds of Examples 2, 3, 4, 5, and 6 were measured in this assay run substantially as above to have human intestinal hydrolysis relative to Internal Prodrug Compound A of 61% (n=3, SD=11.1), 53% (n=3, SD=11.9), 45% (n=1), 35% (n=2; 34.1, 35.2), and 2% (n=1), respectively. These results demonstrate that prodrug compounds within the scope of the present invention are hydrolyzed in the human intestine.

In Vitro Human Liver S-9 Homogenate Hydrolysis Assay

Liver S9 fractions are obtained from Xenotech LLC (Lenexa, Mo.). The lot is from a pool of two donors, one male and one female. The liver S9 fraction is prepared and diluted using a homogenization buffer consisting of 50 mM Tris, pH 7.4 at 4° C. and 150 mM potassium chloride without EDTA. Prodrug compounds are incubated in the liver homogenate for 2 hours at 37° C., after which the concentration of compound is determined by LC/MS/MS. Hydrolysis of Clopidogrel to Clopidogrel Carboxylic Acid is utilized as an assay positive control.

Incubations are conducted in 96-well format and all prodrug compounds are run in duplicate on each day. Stock prodrug compound solutions are prepared in water at a concentration of 1 mM. Human liver S9 fraction is diluted to a final protein concentration of 0.5 mg/ml in 100 mM PBS buffer, pH 7.4.

A 200 μL aliquot of 0.5 mg/ml human liver S-9 homogenate and 196 μL of 100 mM PBS buffer are placed in a 96-well plate in a 37° C. water bath. Using a 96-well pipettor, 4 μL of the 1 mM prodrug solution is transferred into the homogenate. To ensure hydrolysis is not due to chemical instability, prodrug compounds are also incubated with PBS buffer alone without liver S-9 Immediately after addition of the prodrug compound (time zero) and after 1 hour incubation, 50 μL samples of the incubation mixture are removed using an automated disposable simultaneous 96-well pipettor and added directly to 200 μL of methanol quench solution containing 100 ng/ml of Internal Standard. The samples are then centrifuged at 3500 rpm for 5 minutes at 10° C. The supernatant (200 uL) is transferred to a final 96 well PCR plate and sealed for analysis by LC/MS/MS.

LC/MS/MS quantification of compound formed during the incubation is performed on a Sciex API 4000, Analyst version 1.4.2, TurboIonSpray, positive ionization, and Selected Reaction Monitoring (SRM). The HPLC column used is a Waters Atlantis® T3 (20×2.1 mm, 5 μm) at ambient temperature with a mobile phase flow rate of 1.0 mL/min. Mobile phase A is 1000:5 water:heptafluorobuteric acid and mobile phase B is 1:1 methanol/glacial acetic acid. A mobile phase gradient is utilized starting mobile phase ratio A/B of 99.9/0.1 and finishing at 1/99.

Concentrations of hydrolyzed compound in the incubation mixtures are determined from standard curves prepared by replicate two-fold dilution starting at 10 μM in 100 mM PBS pH 7.4 and subsequently quenched with methanol-internal standard solution identical to the samples. Averages and standard deviations are calculated using Microsoft® Office Excel® 2007. Final values are presented as a molar percentage of compound formed relative to prodrug compound concentration added. Hydrolysis of Clopidogrel to Clopidogrel Carboxylic Acid is used as the positive control and averages 73.0% (n=27).

The compounds of Examples 2, 3, 5, 6, and 7 are measured in this assay run substantially as above to have human liver S9 hydrolysis of 1% (n=1), 8% (n=1), 0.4% (n=1), 9% (n=2; 4.4, 13.6), and 29% (n=1), respectively. These results demonstrate that prodrug compounds within the scope of the present invention are hydrolyzed in the human liver.

The data demonstrate that amino acid prodrug compounds within the scope of the present invention inhibit the uptake of the PepT1 substrate GlySar as good as or better than cefadroxil and cephalexin (Zhang et al, 2004. JPET 310:437-445), which is predictive of human oral absorption via the PepT1 transporter. In addition to prodrug compound absorption, upon entering the body, prodrug compound hydrolysis in order to yield the active compound is essential. The present in vitro hydrolysis studies demonstrate that amino acid prodrug compounds within the scope of the present invention can be hydrolyzed by human intestine. Hydrolysis of diester prodrug compounds occur in human liver homogenates demonstrating that diester prodrug compounds within the scope of the present invention hydrolyze in humans following oral exposure. Together these data predict that amino acid prodrug compounds and diester prodrug compounds within the scope of the present invention are hydrolyzed in humans.

We claim:
1. A compound of the formula

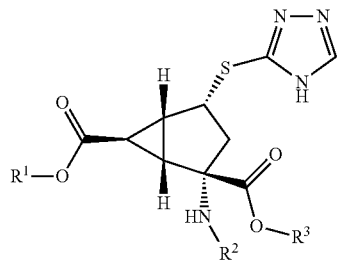

wherein
$R^1$ is hydrogen, $R^2$ is hydrogen, and $R^3$ is hydrogen;
$R^1$ is hydrogen, $R^2$ is (2S)-2-aminopropanoyl, and $R^3$ is hydrogen;
$R^1$ is hydrogen, $R^2$ is (2S)-2-amino-4-methylsulfanyl-butanoyl, and $R^3$ is hydrogen;
$R^1$ is hydrogen, $R^2$ is (2S)-2-amino-4-methyl-pentanoyl, and $R^3$ is hydrogen;
$R^1$ is hydrogen, $R^2$ is 2-aminoacetyl, and $R^3$ is hydrogen;
$R^1$ is benzyl, $R^2$ is hydrogen, and $R^3$ is benzyl; or
$R^1$ is (2-fluorophenyl)methyl, $R^2$ is hydrogen, and $R^3$ is (2-fluorophenyl)methyl;
or a pharmaceutically acceptable salt thereof.

2. The compound according to claim 1 which is (1R,2S,4R,5R,6R)-2-amino-4-(4H-1,2,4-triazol-3-ylsulfanyl)bicyclo[3.1.0]hexane-2,6-dicarboxylic acid, or a pharmaceutically acceptable salt thereof.

3. The compound according to claim 2 which is (1R,2S,4R,5R,6R)-2-amino-4-(4H-1,2,4-triazol-3-ylsulfanyl)bicyclo [3.1.0]hexane-2,6-dicarboxylic acid.

4. The compound according to claim 1 which is (1R,2S,4R,5R,6R)-2-[[(2S)-2-aminopropanoyl]amino]-4-(1H-1,2,4-triazol-3-ylsulfanyl)bicyclo[3.1.0]hexane-2,6-dicarboxylic acid, or a pharmaceutically acceptable salt thereof.

5. The compound according to claim 4 which is (1R,2S,4R,5R,6R)-2-[[(2S)-2-aminopropanoyl]amino]-4-(1H-1,2,4-triazol-3-ylsulfanyl)bicyclo[3.1.0]hexane-2,6-dicarboxylic acid hydrochloride.

6. The compound according to claim 1 which is (1R,2S,4R,5R,6R)-2-[[(2S)-2-amino-4-methylsulfanyl-butanoyl]amino]-4-(4H-1,2,4-triazol-3-ylsulfanyl)bicyclo[3.1.0]hexane-2,6-dicarboxylic acid, or a pharmaceutically acceptable salt thereof.

7. The compound according to claim 6 which is (1R,2S,4R,5R,6R)-2-[[(2S)-2-amino-4-methylsulfanyl-butanoyl]amino]-4-(4H-1,2,4-triazol-3-ylsulfanyl)bicyclo[3.1.0]hexane-2,6-dicarboxylic acid hydrochloride.

8. The compound according to claim 1 which is (1R,2S,4R,5R,6R)-2-[[(2S)-2-amino-4-methyl-pentanoyl]amino]-4-(4H-1,2,4-triazol-3-ylsulfanyl)bicyclo[3.1.0]hexane-2,6-dicarboxylic acid, or a pharmaceutically acceptable salt thereof.

9. The compound according to claim 8 which is (1R,2S,4R,5R,6R)-2-[[(2S)-2-amino-4-methyl-pentanoyl]amino]-4-(4H-1,2,4-triazol-3-ylsulfanyl)bicyclo[3.1.0]hexane-2,6-dicarboxylic acid hydrochloride.

10. The compound according to claim 1 which is (1R,2S,4R,5R,6R)-2-[(2-aminoacetyl)amino]-4-(4H-1,2,4-triazol-3-ylsulfanyl)bicyclo[3.1.0]hexane-2,6-dicarboxylic acid, or a pharmaceutically acceptable salt thereof.

11. The compound according to claim 10 which is (1R,2S,4R,5R,6R)-2-[(2-aminoacetyl)amino]-4-(4H-1,2,4-triazol-3-ylsulfanyl)bicyclo[3.1.0]hexane-2,6-dicarboxylic acid hydrochloride.

12. The compound according to claim 1 which is dibenzyl (1R,2S,4R,5R,6R)-2-amino-4-(4H-1,2,4-triazol-3-ylsulfanyl)bicyclo[3.1.0]hexane-2,6-dicarboxylate, or a pharmaceutically acceptable salt thereof.

13. The compound according to claim 12 which is dibenzyl (1R,2S,4R,5R,6R)-2-amino-4-(4H-1,2,4-triazol-3-ylsulfanyl)bicyclo[3.1.0]hexane-2,6-dicarboxylate.

14. The compound according to claim 1 which is bis[(2-fluorophenyl)methyl](1R,2S,4R,5R,6R)-2-amino-4-(4H-1,2,4-triazol-3-ylsulfanyl)bicyclo[3.1.0]hexane-2,6-dicarboxylate, or a pharmaceutically acceptable salt thereof.

15. The compound according to claim 14 which is bis[(2-fluorophenyl)methyl](1R,2S,4R,5R,6R)-2-amino-4-(4H-1,2,4-triazol-3-ylsulfanyl)bicyclo[3.1.0]hexane-2,6-dicarboxylate hydrochloride.

16. A compound which is bicyclo[3.1.0]hexane-2,6-dicarboxylic acid, 2-[[(2S)-2-amino-1-oxopropyl]amino]-4-(4H-1,2,4-triazol-3-ylthio)-, monoammonium salt, (1R,2S,4R,5R,6R)—, monohydrate.

17. The compound according to claim 16 which is bicyclo [3.1.0]hexane-2,6-dicarboxylic acid, 2-[[(2S)-2-amino-1-oxopropyl]amino]-4-(4H-1,2,4-triazol-3-ylthio)-, monoammonium salt, (1R,2S,4R,5R,6R)—, monohydrate in crystalline form characterized by a X-ray powder diffraction pattern having peaks at 2θ±0.02 equal to 18.61 and 21.07.

18. A pharmaceutical composition comprising a compound of the formula

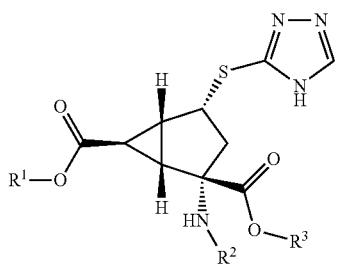

wherein
R[1] is hydrogen, R[2] is hydrogen, and R[3] is hydrogen;
R[1] is hydrogen, R[2] is (2S)-2-aminopropanoyl, and R[3] is hydrogen;
R[1] is hydrogen, R[2] is (2S)-2-amino-4-methylsulfanyl-butanoyl, and R[3] is hydrogen;
R[1] is hydrogen, R[2] is (2S)-2-amino-4-methyl-pentanoyl, and R[3] is hydrogen;
R[1] is hydrogen, R[2] is 2-aminoacetyl, and R[3] is hydrogen;
R[1] is benzyl, R[2] is hydrogen, and R[3] is benzyl; or
R[1] is (2-fluorophenyl)methyl, R[2] is hydrogen, and R[3] is (2-fluorophenyl)methyl;
or a pharmaceutically acceptable salt thereof and a pharmaceutically acceptable carrier, diluent, or excipient.

19. The pharmaceutical composition of claim 18 comprising the compound which is (1 R, 2S,4R,5R,6R)-2-[[(2S)-2-aminopropanoyl]amino]-4-(1H-1,2,4-triazol-3-ylsulfanyl) bicyclo[3.1.0]hexane-2,6-dicarboxylic acid, or a pharmaceutically acceptable salt thereof.

20. A pharmaceutical composition comprising a compound which is bicyclo[3.1.0]hexane-2,6-dicarboxylic acid, 2-[[(2S)-2-amino-1-oxopropyl]amino]-4-(4H-1,2,4-triazol-3-ylthio)-, monoammonium salt, (1R,2S,4R,5R,6R)—, monohydrate and a pharmaceutically acceptable carrier, diluent, or excipient.

21. A method of treating a psychiatric disorder selected from the group consisting of bipolar disorder, schizophrenia, depression, and generalized anxiety disorder, comprising administering to a patient in need thereof an effective amount of a compound of the formula

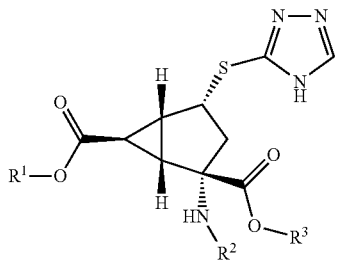

wherein
R[1] is hydrogen, R[2] is hydrogen, and R[3] is hydrogen;
R[1] is hydrogen, R[2] is (2S)-2-aminopropanoyl, and R[3] is hydrogen;
R[1] is hydrogen, R[2] is (2S)-2-amino-4-methylsulfanyl-butanoyl, and R[3] is hydrogen;
R[1] is hydrogen, R[2] is (2S)-2-amino-4-methyl-pentanoyl, and R[3] is hydrogen;
R[1] is hydrogen, R[2] is 2-aminoacetyl, and R[3] is hydrogen;
R[1] is benzyl, R[2] is hydrogen, and R[3] is benzyl; or
R[1] is (2-fluorophenyl)methyl, R[2] is hydrogen, and R[3] is (2-fluorophenyl)methyl;
or a pharmaceutically acceptable salt thereof.

22. The method of claim 21, wherein the psychiatric disorder is bipolar disorder.

23. The method of claim 21, wherein the psychiatric disorder is schizophrenia.

24. The method of claim 21, wherein the psychiatric disorder is depression.

25. The method of claim 21 wherein the psychiatric disorder is generalized anxiety disorder.

26. The method of claim 21 comprising the compound which is (1R,2S,4R,5R,6R)-2-[[(2S)-2-aminopropanoyl]amino]-4-(1H-1,2,4-triazol-3-ylsulfanyl)bicyclo[3.1.0]hexane-2,6-dicarboxylic acid, or a pharmaceutically acceptable salt thereof.

27. The method of claim 26, wherein the psychiatric disorder is bipolar disorder.

28. The method of claim 26, wherein the psychiatric disorder is schizophrenia.

29. The method of claim 26, wherein the psychiatric disorder is depression.

30. The method of claim 26, wherein the psychiatric disorder is generalized anxiety disorder.

31. A method of treating a psychiatric disorder selected from the group consisting of bipolar disorder, schizophrenia, depression, and generalized anxiety disorder, comprising administering to a patient in need thereof an effective amount of a compound which is bicyclo[3.1.0]hexane-2,6-dicarboxylic acid, 2-[[(2S)-2-amino-1-oxopropyl]amino]-4-(4H-1,2,4-triazol-3-ylthio)-, monoammonium salt, (1R,2S,4R,5R,6R)—, monohydrate.

32. The method of claim 31, wherein the psychiatric disorder is bipolar disorder.

33. The method of claim 31, wherein the psychiatric disorder is schizophrenia.

34. The method of claim 31, wherein the psychiatric disorder is depression.

35. The method of claim 31, wherein the psychiatric disorder is generalized anxiety disorder.

* * * * *